(12) United States Patent
Stoddard et al.

(10) Patent No.: US 8,459,132 B2
(45) Date of Patent: Jun. 11, 2013

(54) SYSTEMS AND METHODS FOR MONITORING A SOLID-LIQUID INTERFACE

(75) Inventors: Nathan G. Stoddard, Gettysburg, PA (US); Monte A. Lewis, Montgomery Village, MD (US); Roger F. Clark, Knoxville, MD (US)

(73) Assignee: Advanced Metallurgical Group Idealcast Solar Corp., Wayne, PA (US)

( * ) Notice: Subject to any disclaimer, the term of this patent is extended or adjusted under 35 U.S.C. 154(b) by 0 days.

(21) Appl. No.: 13/061,077

(22) PCT Filed: Aug. 24, 2009

(86) PCT No.: PCT/US2009/054762
§ 371 (c)(1),
(2), (4) Date: Feb. 25, 2011

(87) PCT Pub. No.: WO2010/025107
PCT Pub. Date: Mar. 4, 2010

(65) Prior Publication Data
US 2011/0154879 A1  Jun. 30, 2011

Related U.S. Application Data

(60) Provisional application No. 61/092,606, filed on Aug. 28, 2008.

(51) Int. Cl.
*G01N 33/00* (2006.01)
(52) U.S. Cl.
USPC .......................................................... 73/866

(58) Field of Classification Search
None
See application file for complete search history.

(56) References Cited

U.S. PATENT DOCUMENTS

| 3,646,802 | A | * | 3/1972 | Nolting et al. ................... 374/22 |
|---|---|---|---|---|
| 4,508,460 | A | * | 4/1985 | Croo ................................ 374/16 |
| 5,886,737 | A | | 3/1999 | Hiraishi |
| 6,110,274 | A | * | 8/2000 | Okuno ............................ 117/81 |
| 6,928,869 | B2 | | 8/2005 | Ladirat et al. |
| 7,959,732 | B1 | * | 6/2011 | Buzniak et al. ............... 117/206 |
| 8,030,633 | B2 | * | 10/2011 | Stoddard et al. .............. 250/573 |
| 2005/0193576 | A1 | * | 9/2005 | Hollman et al. ................ 33/286 |

OTHER PUBLICATIONS

Ihara et al., "In Situ Monitoring of Solid-Liquid Interface of Aluminum Alloy Using High-Temperature Ultrasonic Sensor", *Japanese Journal of Applied Physics*, vol. 44, No. 6B, Jun. 24, 2005).
Eyer et al., "Localization of the Solid/Liquid Interface During Directional Solidification of Silicon by a Pulse-Echo Ultrasonic Technique", *Proceedings of the International Photovoltaic Solar Energy Conference*, Kluwer Academic Publishers, NL, vol. CONF. 10, pp. 295-297 (Apr. 8, 1991).

* cited by examiner

*Primary Examiner* — Robert R Raevis
(74) *Attorney, Agent, or Firm* — Barnes & Thornburg LLP; Thomas J. McWilliams; Edward F. Behm, Jr.

(57) ABSTRACT

Systems and methods are provided for monitoring a solid-liquid interface during a casting process. The systems and methods enable determination of the location of a solid-liquid interface during the casting process.

71 Claims, 20 Drawing Sheets

SYSTEMS AND METHODS FOR MONITORING A SOLID-LIQUID INTERFACE

This application claims the benefit of priority from U.S. Provisional Patent Application No. 61/092,606, filed Aug. 28, 2008, the entirety of which is expressly incorporated herein by reference.

This invention was made with U.S. Government support under National Renewable Energy Laboratory (NREL) Subcontract No. ZDO-2-30628-03 under Department of Energy (DOE) Contract No. DE-AC36-98GO10337, awarded by DOE. The U.S. Government has certain rights in this invention.

TECHNICAL FIELD

The present invention generally relates to systems and methods for monitoring a solid-liquid interface. The invention further relates to systems and methods for monitoring the progress of melting and/or solidification of a solid material by monitoring movement of a solid-liquid interface in a partially melted material during, for example, the melt and solidification cycles of a casting process.

BACKGROUND INFORMATION

Recent advances have been made in casting of materials, such as silicon, for applications in the photovoltaic industry. Such advances are described, for example, in copending application Ser. Nos. 11/624,365 and 11/624,411, filed Jan. 18, 2007. Materials, such as those used to form semiconducting substrates or wafers, may include combinations of elements from Groups II-VI, III-V, and IV-IV. In addition, cast metals and especially those reactive metals melted in vacuum may be included as materials. As used herein, the term "material," unless otherwise specified, includes any element or combination of elements from Groups II-VI, III-V, and IV-IV, or those elements from the alkali, alkaline or transition metals and in particular those which may be formed into semiconductor wafers or substrates.

During casting processes, for example, the material may exist simultaneously in multiple phases, such as a molten or partially melted material containing a liquid portion and a solid portion. A solid-liquid interface is located between the liquid and solid portions until the material is completely solidified. As used herein, the term "solid-liquid interface" refers to the boundary between the liquid and solid portions of a material, for example, during either the melting or solidification portions of a casting process. It is understood that the solid-liquid interface may not be exactly two-dimensional, and may have a finite thickness depending on the material being melted/solidified and other processing conditions. Furthermore, the interface may be flat or have a curved shape. Monitoring the solid-liquid interface is important to controlling the melting and solidification processes during casting, so that certain crystal growth characteristics may be achieved, for example. In another example, monitoring the depth of a liquid being held in a container, such as a crucible or holding tank, is important where the height of the column of liquid cannot be determined by only knowing the location of the free liquid surface.

In a known casting procedure for the manufacture of photovoltaic cells, a material, such as silicon feedstock, may be mixed with a dopant for inducing either a positive or negative conductivity type, melted, and then crystallized by either pulling the crystallized material out of a melt zone or solidifying it in place to form ingots. If silicon feedstock is used, these ingots may be monocrystalline silicon (via the Czochralski (CZ) or float zone (FZ) methods), or cast into blocks or "bricks" of monocrystalline silicon, multi-crystalline silicon or polycrystalline silicon, depending on the grain size of the individual silicon grains. As used herein, the term "cast" means that the silicon is formed by cooling a molten material in a mold or vessel used to hold the molten material. As used herein, the term "monocrystalline silicon" refers to a body of single crystal silicon, having one consistent crystal orientation throughout. Further, "conventional multi-crystalline silicon" refers to crystalline silicon having cm-scale grain size distribution, with multiple randomly oriented crystals located within a body of silicon. As used herein, however, the term "geometrically ordered multi-crystalline silicon" (hereinafter abbreviated as "geometric multi-crystalline silicon") refers to crystalline silicon, having cm-scale grain size distribution of geometrically shaped crystals, with multiple ordered crystals located within a body of silicon. Further, as used herein, the term "poly-crystalline silicon" refers to crystalline silicon with micron order grain size and multiple grain orientations located within a given body of silicon. For example, the grains are typically an average of about submicron to submillimeter in size (e.g., individual grains may not be visible to the naked eye), and grain orientation distributed randomly throughout. In the casting procedure described above, the ingots or blocks are cut first into bricks with the proper cross-section, and then into thin substrates, also referred to as wafers, by known slicing or sawing methods. These wafers may then be processed into photovoltaic cells.

Conventional monocrystalline silicon for use in the manufacture of photovoltaic cells is generally produced by the CZ or FZ methods, both being processes in which a cylindrically shaped boule of crystalline silicon is produced. For a CZ process, the boule is slowly pulled out of a pool of molten silicon. For a FZ process, solid material is fed through a melting zone and re-solidified on the other side of the melting zone. A boule of monocrystalline silicon, manufactured in these ways, contains a radial distribution of impurities and defects, such as rings of oxygen-induced stacking faults (OSF) and "swirl" defects of interstitial or vacancy clusters. These defects are fairly well understood, and monocrystalline silicon is generally a preferred source of silicon for producing photovoltaic cells, because it can be used to produce high efficiency solar cells. Monocrystalline silicon is, however, more expensive to produce than conventional multi-crystalline silicon, using known techniques such as those described above.

Conventional multi-crystalline silicon for use in the manufacture of photovoltaic cells is generally produced by a casting process. Casting processes for preparing conventional multi-crystalline silicon are known in the art of photovoltaic technology. Briefly, in such processes, molten silicon is contained in a crucible, such as a fused silica or quartz crucible, and is cooled in a controlled manner to permit the crystallization of the silicon contained therein. The block of multi-crystalline silicon that results is generally cut into bricks having a cross-section that is the same as or close to the size of the wafer to be used for manufacturing a photovoltaic cell, and the bricks are sawn or otherwise cut into such wafers. The multi-crystalline silicon produced in such a manner is an agglomeration of crystal grains where, within the wafers made therefrom, the orientation of the grains relative to one another is nearly random, although some orientations are preferred. Photovoltaic cells made from multi-crystalline silicon generally have lower efficiency compared to equivalent photovoltaic cells made from monocrystalline silicon, due to a higher concentration of grain boundary and dislocation defects. However, because of the relative simplicity and lower costs for manufacturing conventional multi-crystalline silicon, as well as effective defect passivation in cell processing, multi-crystalline silicon is a more widely used form of silicon for manufacturing photovoltaic cells.

Recently, high quality geometrically ordered multi-crystalline silicon has been produced by a casting process, yielding large volumes of cast geometrically ordered multi-crystalline silicon that does not have a random distribution of grains therein. Additionally, high quality monocrystalline silicon has also been produced by a casting process, yielding large volumes of cast monocrystalline silicon that is free of both the high levels of dislocations and grain boundaries found in multicrystalline cast silicon and the radial distribution of defects and impurities present in the CZ and FZ methods. See, for example, copending U.S. patent application Ser. Nos. 11/624,365 and 11/624,411.

SUMMARY OF THE INVENTION

In accordance with the systems and methods described above, there is provided a system for monitoring a solid-liquid interface, comprising: a vessel configured to contain an at least partially melted material having a solid-liquid interface; and an apparatus attached to the vessel and including: a rod configured to measure a location of the solid-liquid interface; a pinion; a rack having a first portion of an outer surface configured to engage the pinion, and to at least partially enclose the rod; a tube configured to at least partially enclose the rack; a rotating wheel configured to contact a second portion of the outer surface of the rack; a motor configured to drive the pinion; and a controller configured to control the motor and monitor at least one parameter of the solid-liquid interface.

In accordance with the systems and methods described above, there is also provided a system for monitoring a solid-liquid interface, comprising: a vessel configured to contain an at least partially melted material having a solid-liquid interface between the solid and liquid portions; and an apparatus attached to the vessel and including: a rod configured to measure a location of the solid-liquid interface; a tube configured to at least partially enclose the rod; a plurality of rotating wheels configured to contact an outer surface of the rod; a motor configured to drive at least one of the plurality of rotating wheels; and a controller configured to control the motor and monitor at least one parameter of the solid-liquid interface.

In accordance with the systems and methods described above, there is also provided a method of monitoring a solid-liquid interface of an at least partially melted material with an apparatus including a rod, a rack at least partially enclosing the rod, and a pinion engaged with the rack, the method comprising: extending the rod to contact the solid-liquid interface; stopping the rod when the rod contacts the solid-liquid interface based on a threshold input; measuring a location of the rod when the rod is stopped; retracting the rod to a predetermined location; and calculating at least one parameter associated with the solid-liquid interface based on at least the measured location of the rod when the rod is stopped.

In accordance with the systems and methods described above, there is also provided a method of monitoring a solid-liquid interface of an at least partially melted material contained in a vessel with an apparatus including a rod, a tube at least partially enclosing the rod, and a plurality of rotating wheels, the method comprising: extending the rod to contact the solid-liquid interface; stopping the rod when the rod contacts the solid-liquid interface based on a threshold input; measuring a location of the rod when the rod is stopped; retracting the rod to a predetermined location; and calculating at least one parameter associated with the solid-liquid interface based on at least the measured location of the rod when the rod is stopped.

In accordance with the systems and methods described above, there is also provided an apparatus for measuring a position of a solid-liquid interface, comprising: a rod having suitable purity and high-temperature mechanical integrity; an automatic position control and measurement device for positioning the rod; and a vacuum-tight housing for containing at least one element of the apparatus.

Additional features and advantages of the invention will be set forth in the description that follows, being apparent from the description or learned by practice of embodiments of the invention. It is to be understood that both the foregoing general description and the following detailed description are exemplary and explanatory, and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention. For illustration purposes, none of the following drawings are to scale. In the drawings.

DESCRIPTION OF THE EMBODIMENTS

Figure 1:
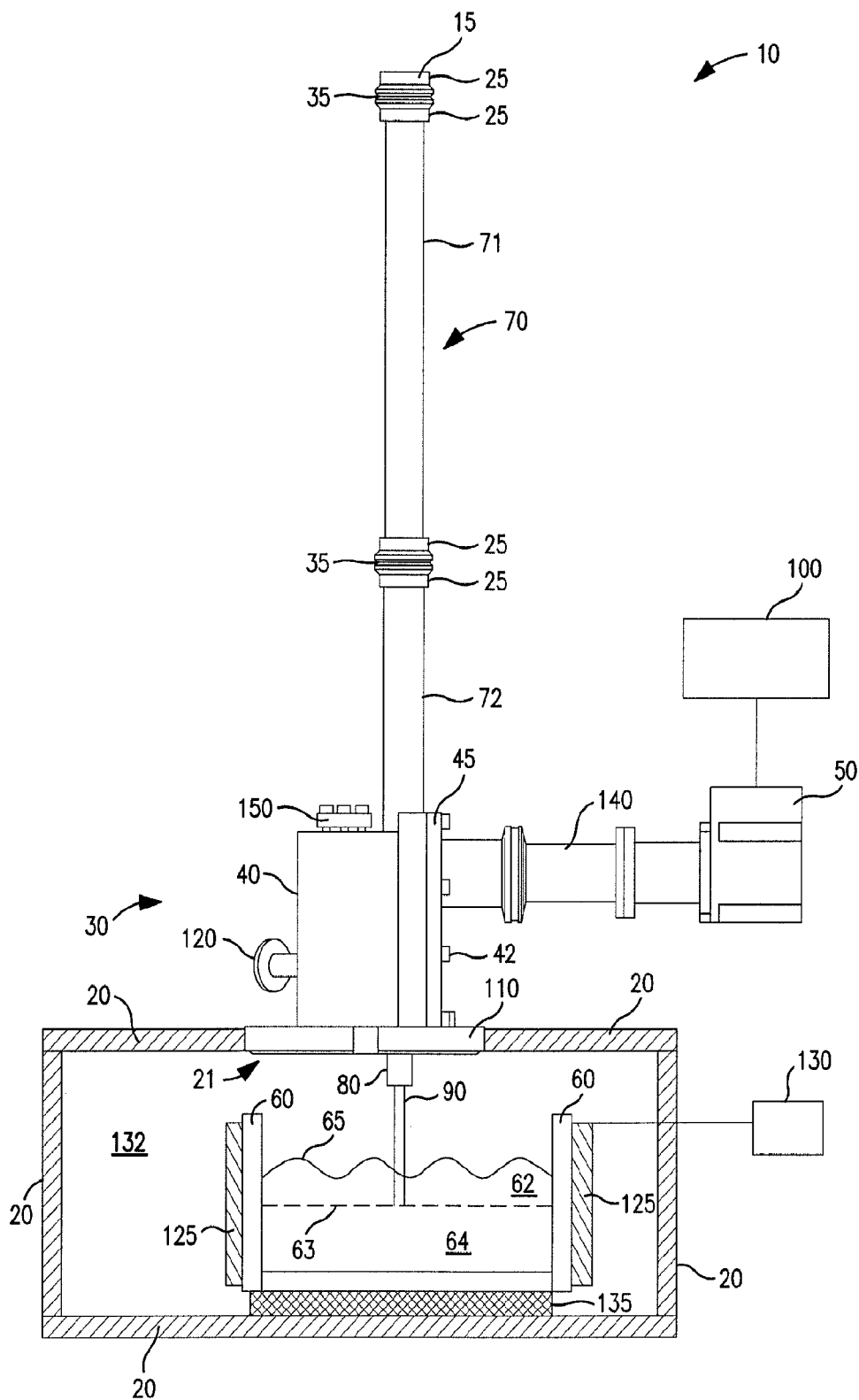
FIG. 1 illustrates, in cross-section, an exemplary system for monitoring a solid-liquid interface in a partially melted material, according to an embodiment of the present invention.

Reference will now be made in detail to embodiments of the present invention, examples of which are illustrated in the accompanying drawings. Wherever possible, the same or similar reference numbers will be used throughout the drawings to refer to the same or like parts.

In embodiments consistent with the invention, the crystallization of a molten material, such as silicon, is conducted by a casting process. A casting process may be defined as a process where material is melted and then solidified in a mould or crucible. The casting process may be implemented in different ways, including using one or more seed crystals. As disclosed herein, such a casting process may be provided so that the size, shape, and orientation of crystal grains in the cast body of crystallized material is controlled. In general, the casting process requires accurate monitoring of the solid-liquid interface and its movement during casting in order to accurately control solidification and to ensure a final product that is substantially free of, or is free of, defects. By way of example, solidification of a material during a casting process can take place in a crucible, where solidification is initiated from at least one wall of the crucible, and not through a cooled foreign object drawing silicon out of the crucible. The crucible may have any suitable shape, such as a cup, a cylinder, or a box. Further, consistent with an embodiment of the present invention, the mold, vessel, or crucible includes at least one "hot side wall" surface in contact with the molten material. As used herein, the term "hot side wall" refers to a surface that is isothermal with or hotter than the molten material that it contacts. Preferably, a hot side wall surface remains fixed during processing of the material.

Consistent with one embodiment of the present invention, solidification during a casting process can be accomplished by positioning a desired collection of crystalline "seeds" in, for example, the bottom of a vessel, such as a quartz, fused silica, or graphite crucible that can hold a molten material. As used herein, the term "seed" refers to a geometrically shaped piece of material with a desired crystal structure, wherein at least one cross-section has a geometric, polygonal, shape, preferably having a side that conforms to a surface of a vessel in which it may be placed. For example, in a casting process for silicon, such a seed can be either a monocrystalline piece of silicon or a piece of geometrically ordered multi-crystalline silicon. As used herein, the term "continuous monocrystalline silicon" refers to single crystal silicon, where the body of silicon is one homogeneous body of silicon with a consistent crystal orientation throughout and not smaller pieces of silicon joined together to form a larger piece of silicon. Further, as used herein, the term "continuous geometric multi-crystalline silicon" refers to geometric multi-crystalline silicon where the body of silicon is one homogeneous body of geometric multi-crystalline silicon and not smaller pieces of silicon joined together to form a larger piece of silicon. Consistent with an embodiment of the present invention, a seed may have a top surface that is parallel to its bottom surface, although this does not have to be the case.

During a casting process of silicon, for example, molten silicon is allowed to cool and crystallize in the presence of the seeds, preferably in a manner such that the cooling of the molten silicon is conducted so that the crystallization of the molten silicon starts at or below the level of the original top of the solid seeds and proceeds away, preferably upwards away, from the seeds. The solid-liquid interface at an edge of the molten silicon conforms to a cooling surface of the vessel, such as a surface in a crucible, in which it is being cast. The solid-liquid interface between the molten silicon and the crystallized silicon can be maintained substantially flat throughout part or all of the casting process. The solid-liquid interface at each of the edges of the molten silicon is controlled during the cooling so as to move in a direction that increases a distance between the molten silicon and the silicon seed crystal while preferably maintaining a substantially flat solid-liquid interface. Although this example described casting of silicon, one of ordinary skill in the art will recognize that other materials may be cast using the method discussed above.

Therefore, consistent with the present invention, the solid-liquid interface may at some point conform to the shape of a cooled surface of the vessel. For example, with a flat-bottomed crucible, the solid-liquid interface may remain substantially flat, with the solid-liquid interface having a controlled profile. The solid-liquid interface can be controlled so that its radius of curvature decreases as one moves from the edge to the center. Alternatively, the solid-liquid interface can be controlled to maintain an average radius of curvature of at least half the width of the vessel. For example, consistent with the present invention, the solid-liquid interface can be controlled to maintain an average radius of curvature of at least twice the width of the vessel. The solid can have a slightly convex interface with a radius of curvature at least about four times the width of the vessel. For example, the solid-liquid interface can have a radius of curvature generally greater than 2 m in a 0.7 m square crucible, more than twice the horizontal dimension of the crucible, and preferably about 8× to about 16× a horizontal dimension of the crucible.

Monitoring the solid-liquid interface permits controlled heating and/or cooling of a portion of the material to be crystallized in order to control the location and movement of a solid-liquid interface during the casting process. Consistent with the present invention, this monitoring may be performed by measuring a location of the solid-liquid interface, which subsequently may be used to calculate a rate of change in the location of the solid-liquid interface, i.e., the melting or the solidification rate of the partially melted material during a casting process. Typically, a rod may be used to measure the location of the solid-liquid interface by dipping into the liquid portion until reaching the solid-liquid interface. Conventionally, using a rod to measure the location of the solid-liquid interface is performed manually by an operator, for example. The disclosed invention provides a system to automate the monitoring process.

Referring to FIG. 1, an exemplary system 10 for monitoring a solid-liquid interface of an at least partially melted material during a casting process is shown in cross-section. System 10 may include a vessel 20 containing, in part, a crucible 60. Crucible 60 may contain an at least partially melted material including a solid portion 64 (also referred to as "a solid material 64"), a liquid portion 62 (also referred to as "a liquid material 62"), and a solid-liquid interface 63 located at the interface of solid portion 64 and liquid portion 62. Crucible 60 may be of any suitable shape, such as flat-bottomed or cup-shaped, though it is depicted for illustration purposes as rectangular-shaped. Crucible 60 may be open on at least one side, the open side preferably facing a port 21 of vessel 20, which is located above the open side of crucible 60. Port 21 may be covered by a removable plate (or cover) 110. Removable plate 110 may be connected to the rest of vessel 20, for example, by one or more clasps, screws, bolts, etc.

Still referring to FIG. 1, heating elements 125 may be included in vessel 20, preferably surrounding one or more sides of crucible 60. Heating elements 125 may be resistive heating elements, for example, and may surround crucible 60 or may be positioned over top and under the bottom of the crucible. Alternatively, heating elements 125 may be individual heating elements of any desired size, shape, or quantity sufficient to heat the contents of crucible 60. Preferably, heating elements 125 may be a series of concentric rings or individual bars/strips/blocks, such that each of the elements 125 may be controlled independently to enable localized heating of a specific portion of crucible 60. Heating elements 125 may be, for example, a resistive heating element or elements, such as graphite or silicon carbide, electromagnetic (EM) heating coils, or any other suitable heating apparatus. Heating elements 125 are preferably controlled, electronically or otherwise, by a heating controller 130. For example, heating controller 130 may be a programmable electronic device, either self-contained or part of an overall computer control system, for providing electric current to heating elements 125.

Still referring to FIG. 1, a solid heat sink 135 may be disposed at the bottom of vessel 20, and configured to be in contact with crucible 60 for radiating heat to water-cooled walls (not shown). For example, heat sink 135 may be a solid block of graphite, and may preferably have dimensions as large or larger than the bottom of the crucible. Consistent with an exemplary embodiment of the invention, heat sink 135 can be approximately 66 cm by 66 cm by 20 cm, when used with a crucible having a bottom surface that is approximately 66 cm by 66 cm. The side walls of crucible 60 are, preferably, water cooled and insulated from a hot zone 132, such that solidification of any material melted therein begins at the bottom of the crucible 60. Alternatively, it is possible to have heat sink 135 located on one or more other surfaces of crucible 60, in combination with alternatively placed heating elements 125. Consistent with certain embodiments of the invention, heating elements 125 may alternatively be located at different locations with respect to the bottom of crucible 60. Heating element 125 may also be referred to as "hot side wall surface 125." Further, by selectively controlling heating elements 125, heating controller 130 may be used to produce a temperature gradient (not shown) inside crucible 60. Using a combination of heating elements 125 and heating controller 130, and optionally using heat sink 135, any desired temperature gradient may be produced in crucible 60.

As further illustrated in FIG. 1, solid material 64 is added to crucible 60. Solid material 64 may be, for example, any suitable solid material for use in a casting process. For example, if silicon is being cast, solid material 64 may comprise silicon feedstock. In embodiments consistent with the invention, such feedstock, for example, may be placed on top of one or more seed crystals (not shown), such as a mono crystalline piece or silicon or a piece of geometrically ordered multi-crystalline silicon. Moreover, depending on the casting process, solid material 64 may completely or partially fill crucible 60. When controller 130 controls the heating of one or more of heating elements 125, part or all of the solid material 64 can be melted.

In the example illustrated in FIG. 1, melting may begin near the top of crucible 60, producing a region of liquid material 62 inside crucible 60. Liquid material 62 may have a liquid surface 65, and a solid-liquid interface 63 with the remaining portion of solid material 64. Liquid surface 65 may experience one or more surface waves or disturbances. Alternatively, melting may begin at the bottom of crucible 60, or at any point in between, depending on the desired temperature gradient produced within crucible 60 by heating elements 125. Consistent with embodiments of the invention, liquid material 62 may be above the solid material 64. It may also be possible, however, depending on the material being cast, to have at least a portion of solid material 64 float in or on liquid material 62.

The melting phase of solid material 64 may be closely monitored to track the location of the solid-liquid interface 63. Preferably, the melting phase proceeds until all or almost all of the solid material 64 is completely melted. For example, the heating can be closely controlled such that all of the solid portion 64 does not melt completely, by maintaining a time rate of change of temperature, dT/dt, of about 0.1° C./min or less, as measured on an outside surface of the crucible 60, after reaching the melting temperature of the solid portion 64 elsewhere in the crucible 60. Preferably, in one embodiment, the heating can be closely controlled by maintaining a dT/dt of about 0.05° C./min or less, as measured on an outside surface of the crucible 60, after reaching the melting temperature of solid portion 64 elsewhere in the crucible. For example, consistent with the invention, the temperature can be measured on an outside surface of the crucible 60 between the crucible and heat sink 135.

Still referring to FIG. 1, by measuring the location of solid-liquid interface 63, it is possible to gather information on the progress of melting/crystal growth, for example, the thickness of the remaining solid portion 64 during a melting process. A rod 90 may be used to measure the location of solid-liquid interface 63. For example, rod 90 may be manually extended into vessel 20 and dipped into liquid portion 62 until it reaches solid-liquid interface 63. Since rod 90 may be extended starting from a known location, it is possible to measure the location of solid-liquid interface 63. When such measurements are conducted regularly at preset time intervals, the rate of change of the location of solid-liquid interface 63 may be calculated, which may yield information regarding the speed of melting/crystal growth. With information obtained from the measured location and the calculated rate, the entire melting/crystal growth process may be accurately controlled by controlling heating temperature through heating controller 130. However, manually conducting measurements may be a labor intensive task since measurements may have to be taken, for example, every 10 minutes for more than 24 hours. Location measurements conducted manually may also be prone to error, inaccuracy or malfunction. Furthermore, since the rod must pass through the atmosphere control, it must be sealed by o-rings such that the top of the rod is outside the vacuum while the bottom is inside. The friction from this seal will add to the difficulty of manual measurement.

On the other hand, the entire measurement process may be automated, for example, as implemented in system 10, so that solid-liquid interface 63 may be automatically monitored. System 10 may therefore include an apparatus 30, which may include a mechanism to automate the monitoring process of the solid-liquid interface during casting. The mechanism may include an automatic position control and measurement device for positioning the rod. The automatic position control and measurement device may include an electronic readout (or any suitable means for conveying position and measurement control information to the user or to one or more components of system 10 including apparatus 30). Apparatus 30 may further include removable plate 110, which may be disposed on top of vessel 20 to cover and seal the top of vessel 20. One or more components of system 10, and in particular, apparatus 30, may be contained in a vacuum-tight housing. Apparatus 30 may also include rod 90. Rod 90 may be at least partially enclosed by a rack 80, which may be further at least partially enclosed by a tube 70. Consistent with an embodiment, rack 80 may include a tubular shape, and tube 70 may include a plurality of portions, or segments, such as a first portion 71, and a second portion 72. At least one portion of the plurality portions may be removable to allow access to rack 80 and rod 90 enclosed inside tube 70. While rack 80 and tube 70 are preferably of cylindrical type having circular cross sectional areas, it is contemplated that the cross sectional areas of rack 80 and tube 70 may be of any shape, for example, square, triangular, or polygonal. Tube 70 may include joining components such as a plurality of flanges 25, and a sealing component such as an O-ring component 35, located at the joint section between first portion 71 and second portion 72. In one embodiment, component 35 may be located about ⅔ of the length of tube 70 from a top end 15. In some embodiments, the joint section between first portion 71 and second portion 72 may be located at any suitable portion of the entire tube 70. Flanges 25 may be removable such that first portion 71 may be disassembled, allowing access to rack 80 and rod 90 for inspection, installation, or replacement. Similarly, top end 15 of tube 70 may also include joining components such as flanges 25, and a sealing O-ring component 35. At top end 15, devices such as a glass window (not shown in FIG. 1) may be further mounted for various purposes, which will be shown in later figures.

A housing 40 may be provided to contain a portion of rack 80, tube 70, and rod 90. Rack 80 and tube 70 may be vertically inserted into housing 40 from a top side of housing 40. The bottom of housing 40 may be secured to plate 110, for example, with one or more screws, bolts, clasps, or by welding. Although depicted as having a cubical shape, housing 40 may have any type of shape, such as a cylindrical shape. Housing 40 may include a first and a second chamber separated by a first wall (not shown). On one side of the housing 40, there may be an inlet 120 configured to let fluid flow into housing 40. Housing 40 may include a window mounting structure 150 attached to a top surface of housing 40. Window mounting structure 150 may be used, for example, to mount a glass window. Housing 40 may contain a mechanism (not shown) to move rod 90, and/or rack 80. The mechanism may be driven by a motor 50. Motor 50 may include a motor housing 140. Motor housing 140 may be mounted to a second wall 45 of housing 40. Second wall 45 may be removable, and may be mounted to housing 40 through one or more fastening devices such as a screw, or a bolt 42, and may cover a side of first chamber (not shown). Motor 50 may be controlled by a controller 100, which may be a stand-alone controller or a part of a computer system. Controller 100 may be programmed to automate the movement of rod 90 and thus the monitoring of the entire melting process. In some embodiments, heating controller 130 may be associated with controller 100, or may be integrated with controller 100.

Figure 2:
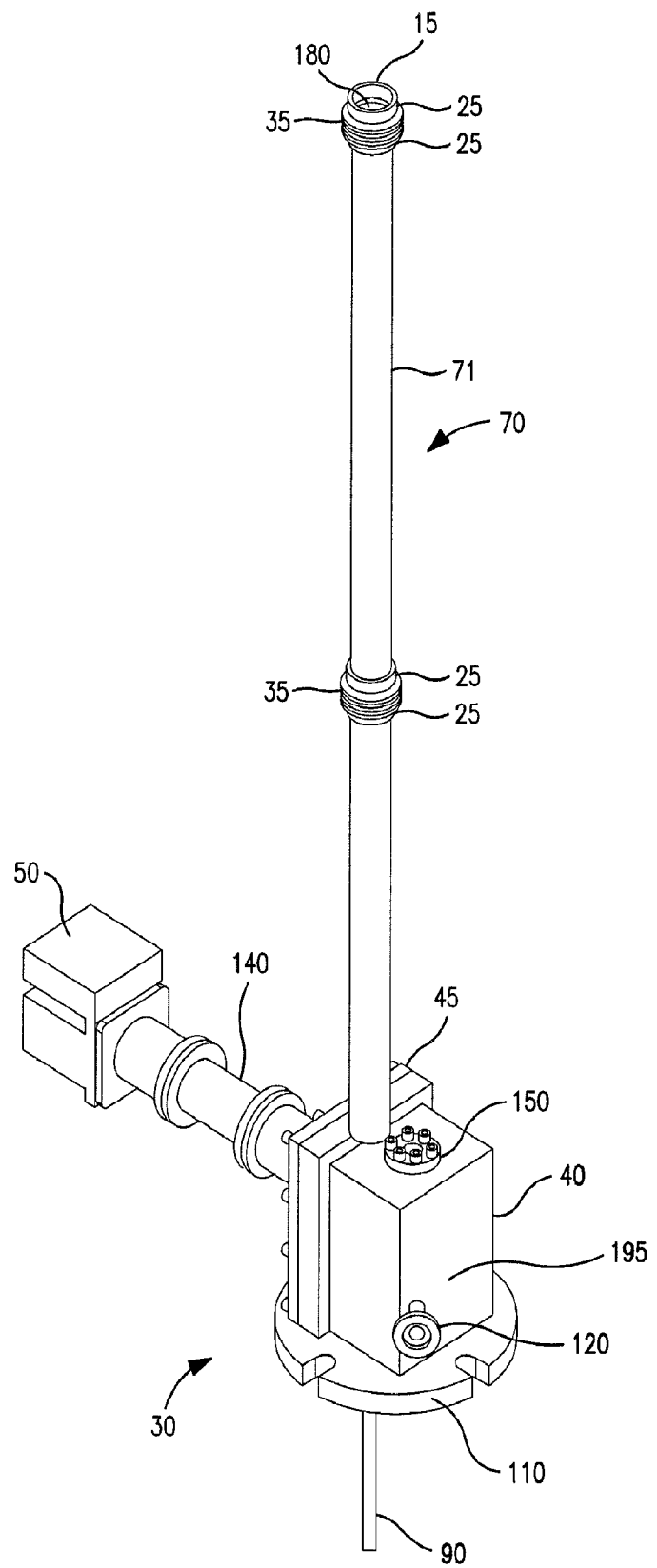
FIG. 2 illustrates a perspective view of an exemplary apparatus employed in a system for monitoring a solid-liquid interface in a partially melted material, according to an embodiment of the present invention.

FIG. 2 provides a perspective view of apparatus 30. It is shown that inlet 120 may be attached, or mounted to an outer surface 195 of housing 40. Most other components shown in FIG. 2 have been illustrated in FIG. 1, therefore, will not be repeated here.

Figure 3:
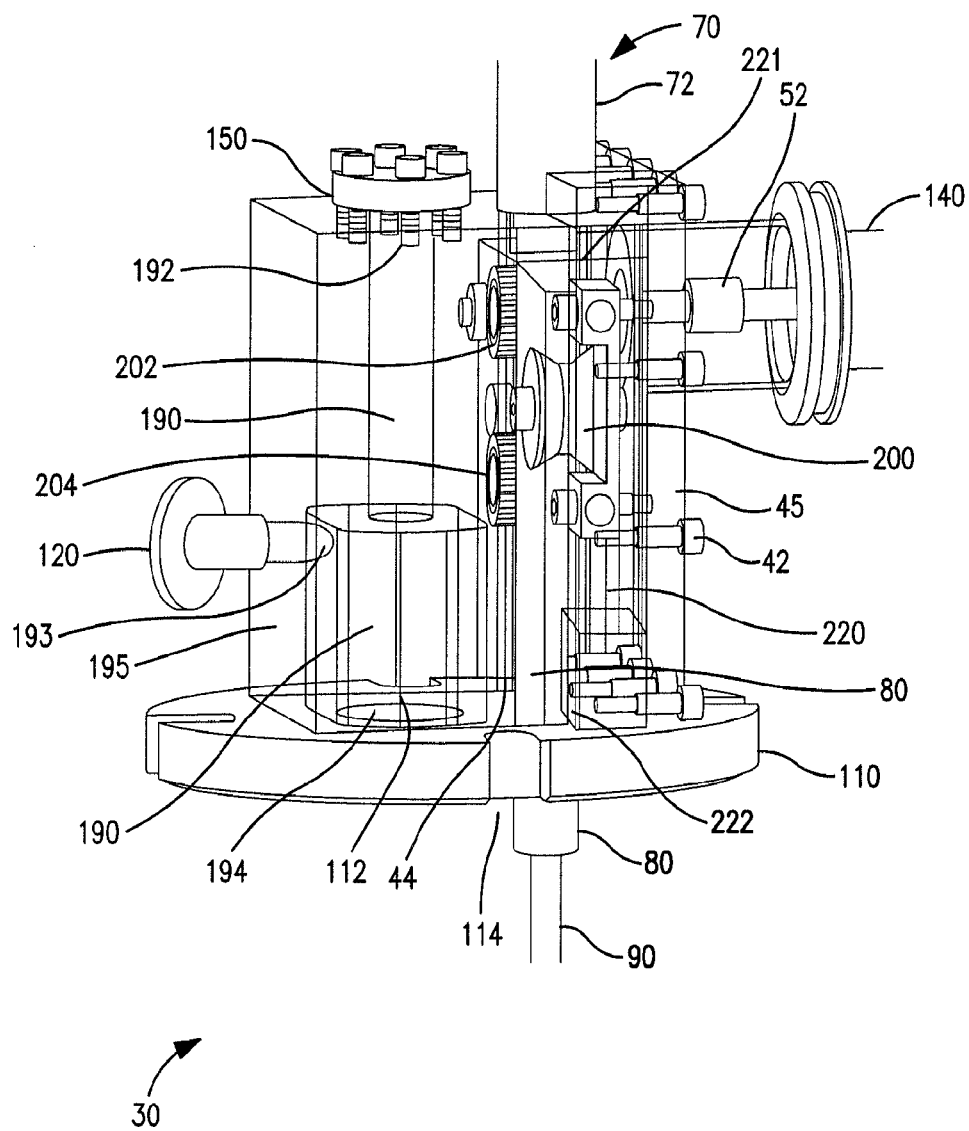
FIG. 3 illustrates a three dimensional cut away view of an exemplary apparatus employed in a system for monitoring a solid-liquid interface in a partially melted material, according to an embodiment of the present invention.

FIG. 3 shows a three dimensional cut away view of the contents of housing 40. Housing 40 may include a first chamber 220 and a second chamber 190, separated by a first wall 44. Second wall 45 may cover a side of first chamber 220, and when removed, may allow access to the contents of first chamber 220. First chamber 220 may contain a rotating wheel 200, a first pinion 202, a second pinion 204, and a portion of rack 80 and rod 90. The first and second pinions 202 and 204 are essentially gears. Consistent with an embodiment, first chamber 220 may also contain a portion of tube 70. First chamber 220 may include a first open port 221, and a second open port 222. Rack 80 may enter first chamber 220 through first open port 221 and extend through the top of first chamber 220 through second open port 222. Second chamber 190 may include a first open port 192 and a second open port 194. Window mounting structure 150 may be mounted adjacent to first open port 192 of second chamber 220. Second open port 194 may be associated with a hollow zone 112 in plate 110. A window (not shown) may be mounted to the window mounting structure 150. Through the window, second chamber and hollow zone 112, an operator may observe the contents of vessel 20. Second chamber 190 may further include a third open port 193 on a side wall having outer surface 195. Inlet 120 attached to outer surface 195 may be connected with third open port 193 so that a fluid, such as a cooling and/or purge gas, for example, argon gas, may flow into second chamber 190 through inlet 120 and third open port 193. Cooling or purge gas inside second chamber 190 may function to reduce temperature of first chamber 220 through first wall 44 between first chamber 220 and second chamber 190. Gases injected through inlet 120 may also help maintain a desired pressure inside second chamber 190, as well as maintain the purity and inertness of the chamber environment.

FIG. 3 also shows a motor shaft 52 enclosed inside motor housing 140. Motor shaft 52 may be mounted through second wall 45 and mounted to first pinion 202 through a hollow zone (not shown) around a center rotating axis of first pinion 202.

Motor 50 may drive at least one of first pinion 202 and second pinion 204 through motor shaft 52.

Figure 4:
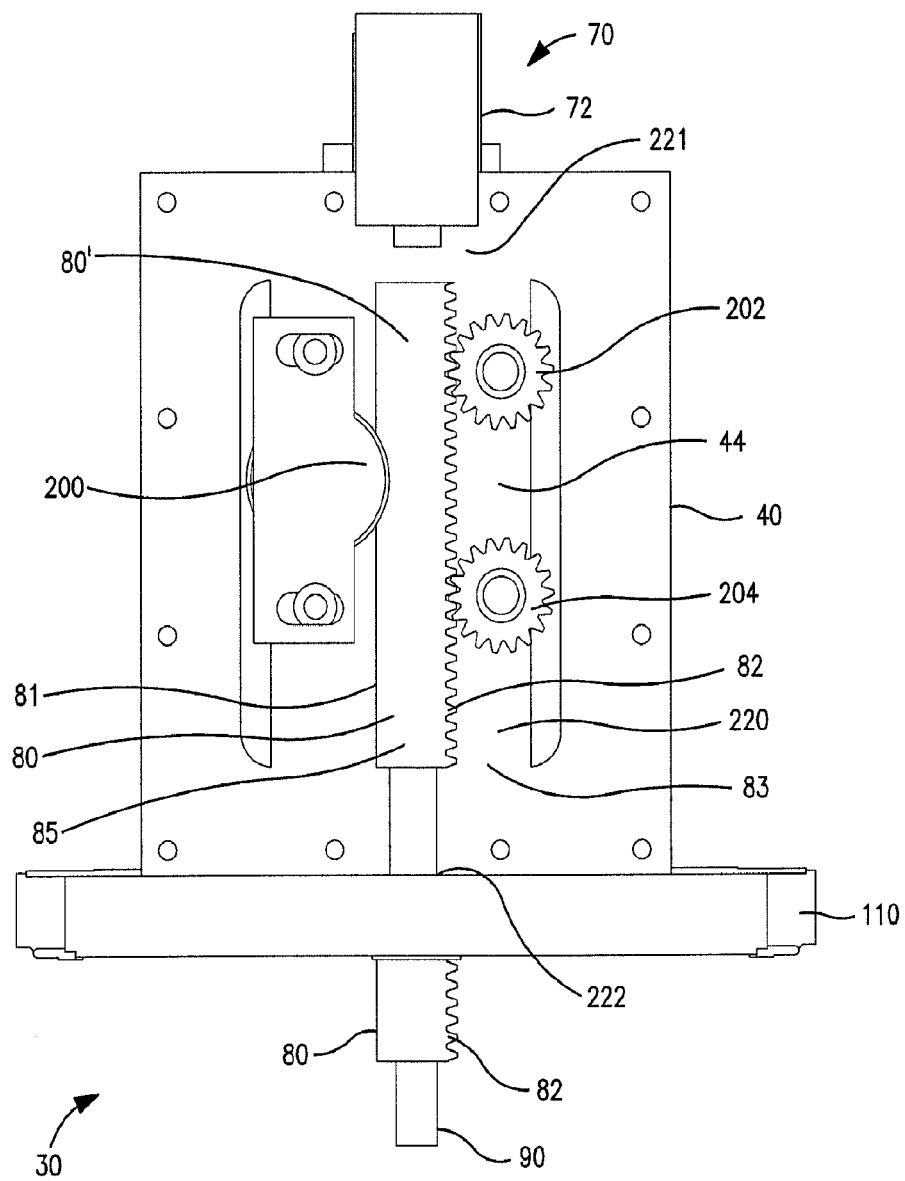
FIG. 4 illustrates a sectional view of an exemplary apparatus employed in a system for monitoring a solid-liquid interface in a partially melted material, according to an embodiment of the present invention.

FIG. 4 illustrates a cross-sectional view of first chamber 220 of apparatus 30, shown in FIG. 3. As depicted in FIG. 4, first chamber 220 may contain a portion 80' of rack 80. Rack 80 may have an outer surface 85. On a first portion 81 of outer surface 85, there may be tooth-shaped features 82 configured to engage with first pinion 202 and second pinion 204. First pinion 202 and second pinion 204 may be disposed on one side of rack 80, and rotating wheel 200 may be disposed on another side of rack 80. Rotating wheel 200 may be any type of rotating wheel known in the art, which may be configured to contact a second portion 83 of outer surface 85. The second portion 83 of outer surface 85 may be opposite to the first portion 81. First pinion 202 may be driven by motor 50 through motor shaft 52 shown in FIG. 3. As first pinion 202 rotates, the rotational motion of the pinion may be translated into vertical motion of rack 80 through contact with tooth-shaped features 82 on rack 80. Since rod 90 may be secured to rack 80, the vertical motion of rack 80 may extend or retract rod 90 to and from vessel 20. Second pinion 204 may or may not be driven by a motor. Second pinion 204 may provide support to rack 80 to prevent non-vertical motion of rack 80, such as, for example, tilting of rack 80. Rotating wheel 200 may also provide support to rack 80 to prevent non-vertical motion to rack 80. In some embodiments, at least one of first and second pinions 202 and 204, and rotating wheel 200, may be mounted on first wall 44 that separates first chamber 220 and second chamber 190. In some embodiments, at least one of first and second pinions 202 and 204, and rotating wheel 200, may be mounted on second wall 45 that removably covers a side of first chamber 220. Lubricant between pinions 202 and 204 and rack 80 may not be needed, although it is contemplated that a graphite lubricant may be used.

Figure 5:
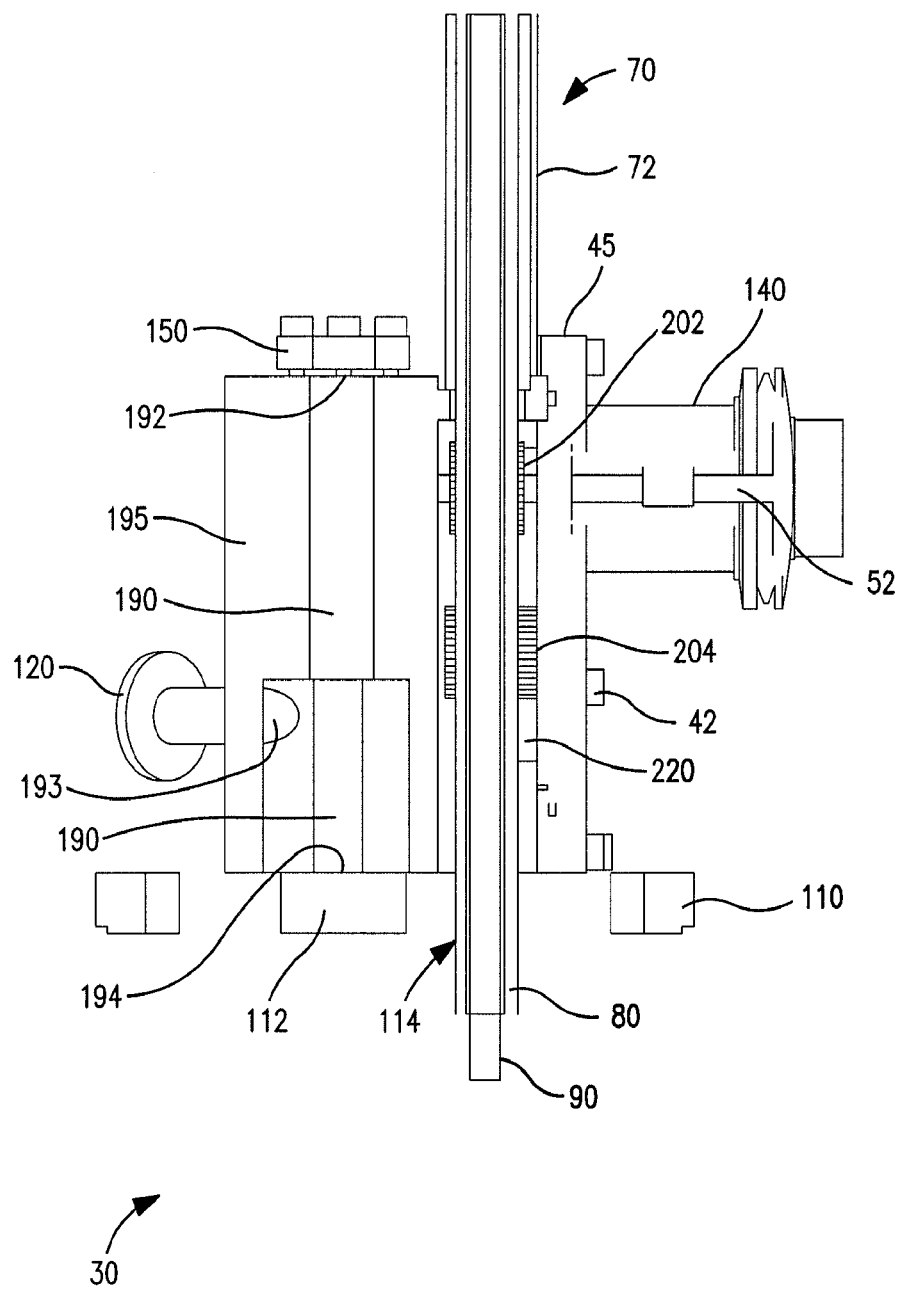
FIG. 5 illustrates a sectional view of an exemplary apparatus employed in a system for monitoring a solid-liquid interface in a partially melted material, according to an embodiment of the present invention.
Figure 6:
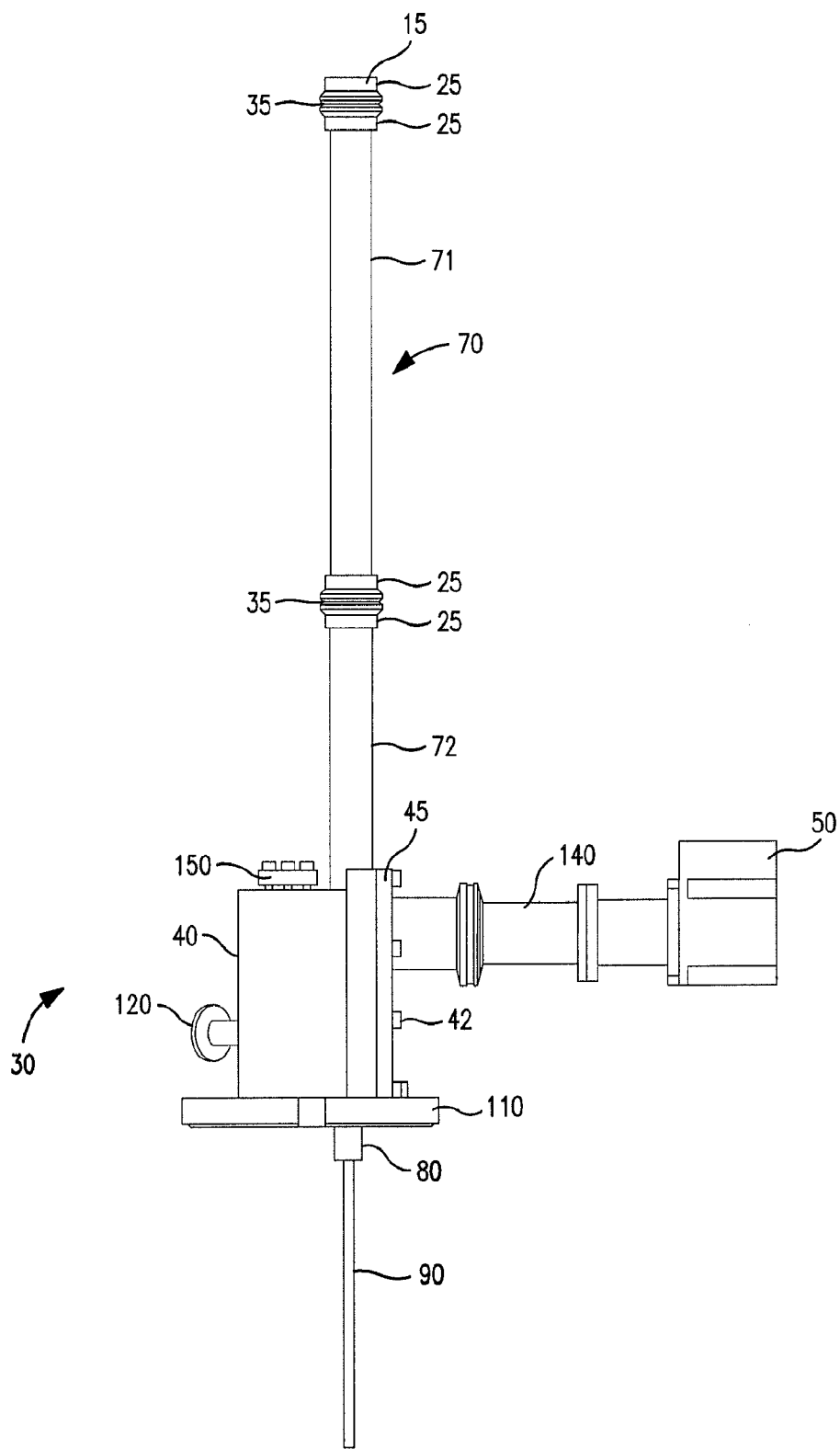
FIG. 6 illustrates a sectional view of an exemplary apparatus employed in a system for monitoring a solid-liquid interface in a partially melted material, according to an embodiment of the present invention.
Figure 7:
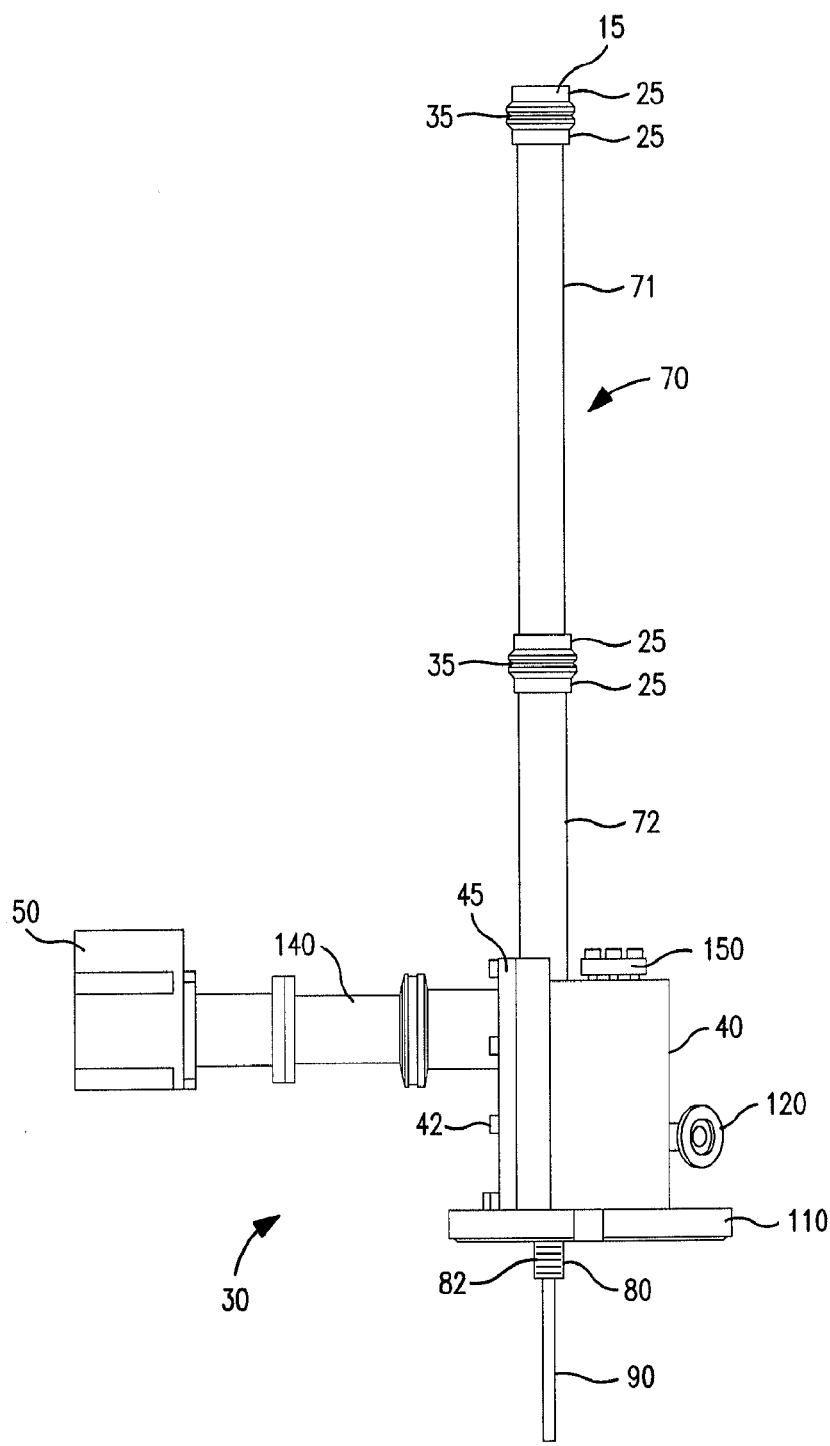
FIG. 7 illustrates a sectional view of an exemplary apparatus employed in a system for monitoring a solid-liquid interface in a partially melted material, according to an embodiment of the present invention.
Figure 8:
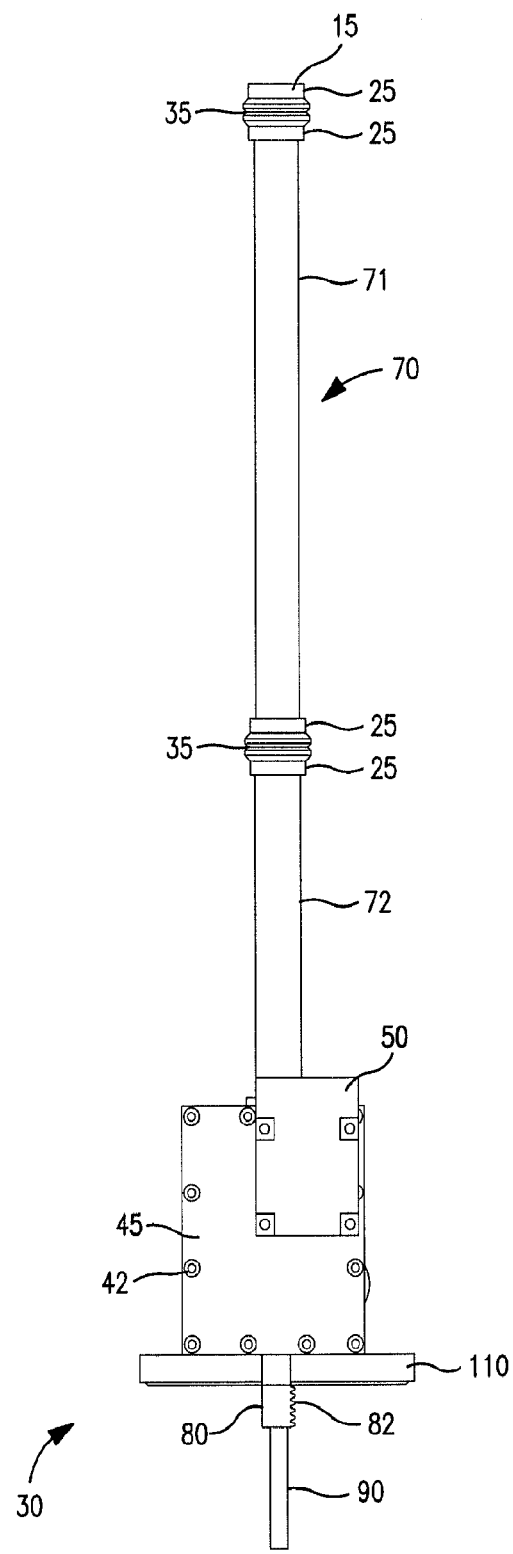
FIG. 8 illustrates a sectional view of an exemplary apparatus employed in a system for monitoring a solid-liquid interface in a partially melted material, according to an embodiment of the present invention.
Figure 9:
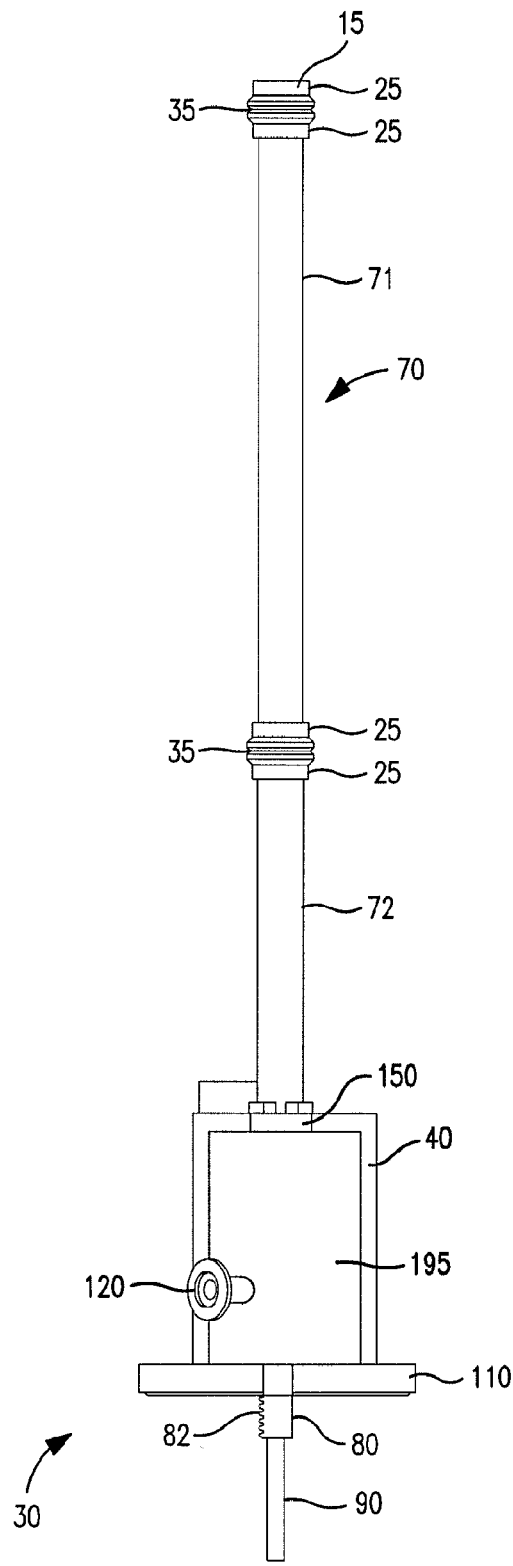
FIG. 9 illustrates a perspective view of the inside of a housing of an exemplary apparatus employed in a system for monitoring a solid-liquid interface in a partially melted material, according to an embodiment of the present invention.

FIG. 5 illustrates another cross-sectional view of apparatus 30. In FIG. 5, a hollow zone 114 is visible in plate 110 associated with second open port 222 shown in FIG. 3. FIG. 6 illustrates a plane view of apparatus 30. FIG. 7 provides another plane view of apparatus 30. FIG. 8 illustrates another plane view of apparatus 30. FIG. 9 provides another plane view of apparatus 30.

Figure 10:
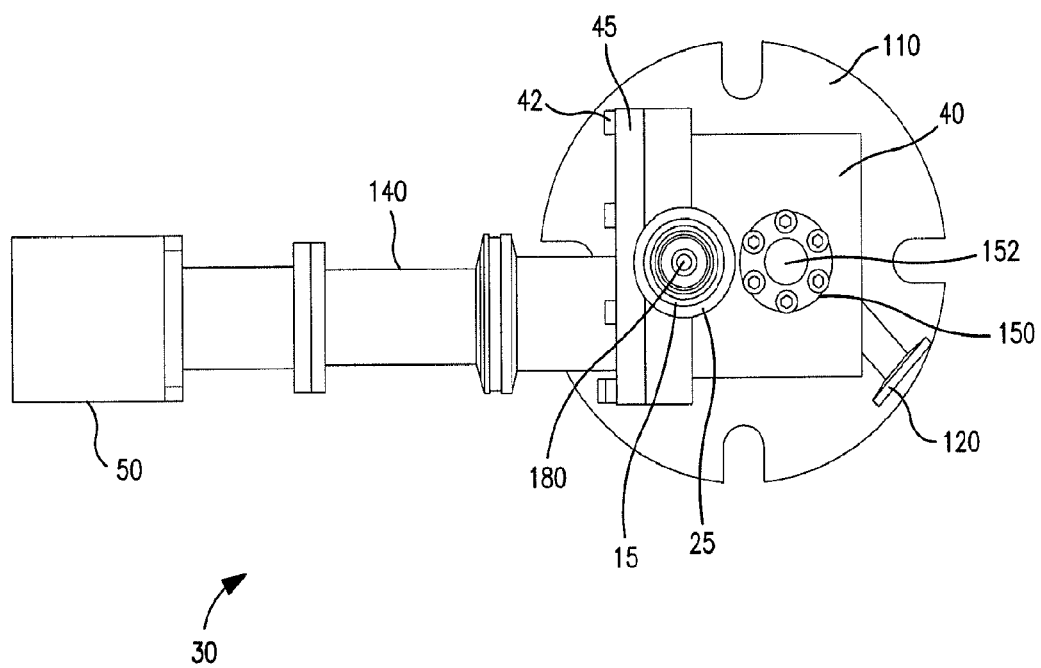
FIG. 10 illustrates, in cross section, an exemplary apparatus employed in a system for monitoring a solid-liquid interface in a partially melted material, according to an embodiment of the present invention.

FIG. 10 illustrates a sectional view from the top of apparatus 30. In FIG. 10, a window 180 is shown mounted at top end 15 of tube 70. Window 180 may be made of glass, or any other suitable material. A second window 152 is shown mounted at window mounting structure 150, which is mounted above second chamber 190 of housing 40. Window 152 may be made of glass or any other suitable material.

Figure 11:
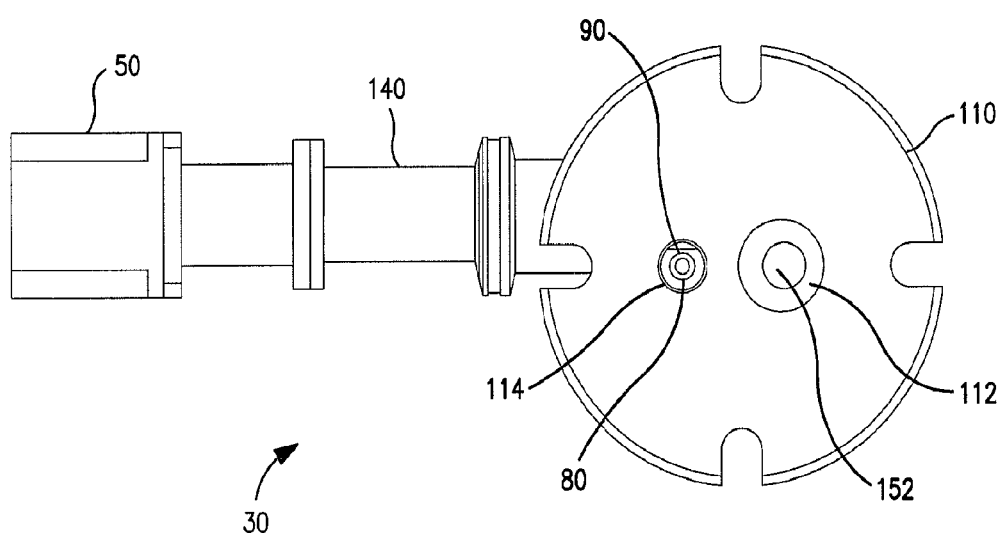
FIG. 11 illustrates, in cross section, an exemplary apparatus employed in a system for monitoring a solid-liquid interface in a partially melted material, according to an embodiment of the present invention.

FIG. 11 illustrates a sectional view from the bottom of apparatus 30. Hollow zone 112 of plate 110 is shown to be associated with window 152 so that the inside of vessel 20 may be observed from window 152 through second chamber 190 and hollow zone 112. Hollow zone 114 of plate 110 is shown to be associated with rack 80 and rod 90. Hollow zone 114 may allow radiation, such as heat, light, or infrared, etc., to be emitted out of vessel 20.

With reference to FIGS. 1-11 above, before taking location measurement of rod 90 to monitor solid-liquid interface 63, system 10 may be calibrated. The purpose of calibration is to establish an origin location for rod 90 so that any further location measurement may reference this origin location. Any fixed point in the path of moving rod 90 may be used to help define the origin location of rod 90, for example, the bottom of vessel 20, the bottom of crucible 60, a plate (not shown) hung from the port 21 of vessel 20 in the path of rod 90, etc.

In the following discussion, the bottom of vessel 20 is used as an exemplary reference point for an exemplary calibration process.

Figure 12:
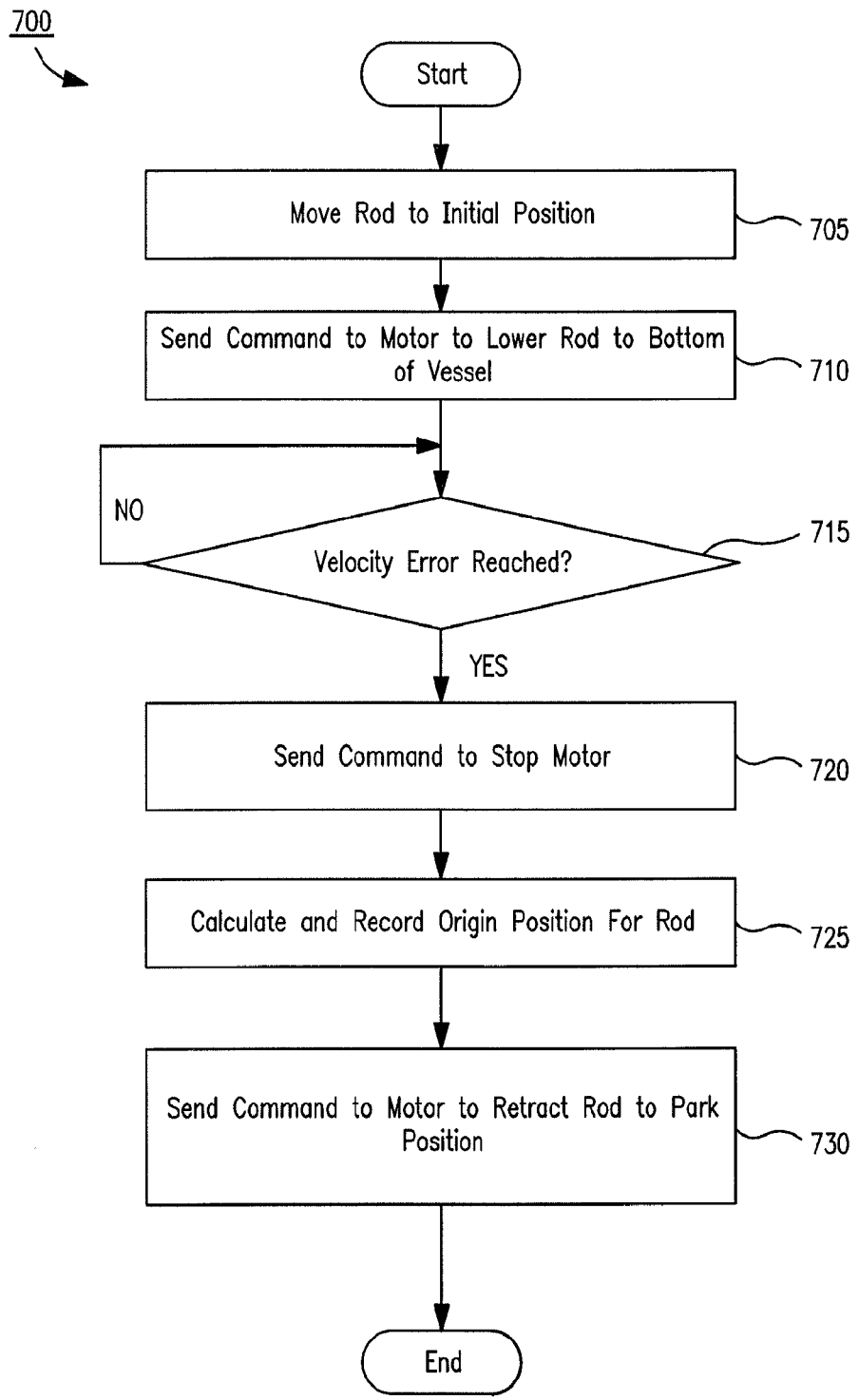
FIG. 12 illustrates an exemplary method for calibrating an apparatus employed in a system for monitoring a solid-liquid interface in a partially melted material, according to an embodiment of the present invention.

FIG. 12 illustrates an exemplary calibration process 700. First, after apparatus 30 is assembled, rod 90 is moved to an initial location (Step 705), for example, a location that is farthest to the bottom of vessel 20. Controller 100 may send a command signal to motor 50 to drive first pinion 202 to lower (or extend) rod 90 toward the bottom of vessel 20 (Step 710). While lowering rod 90, controller 100 may be programmed to record the velocity of motor 50. When rod 90 contacts solid heat sink 135 at the bottom of vessel 20, it will be blocked from moving further, at which point controller 100 may stop motor 50 based on a threshold input, for example, a pre-set velocity error. For example, controller 100 may calculate a velocity error between the tracked motor velocity and a programmed drive velocity, and determine whether the velocity error has reached the pre-set velocity error (Step 715). The pre-set velocity error may be, for example, any reasonable value with a proper unit, for example, 15 counts per second. If the pre-set velocity error has not been reached (NO, Step 715), the motor may continue to drive first pinion 202 until the pre-set velocity error is reached. If the pre-set velocity error has been reached (YES, Step 715), controller 100 may send a command signal to motor 50 to stop the motor (Step 720). The current location of rod 90 is used to calculate the origin (or zero) location of rod 90, which is then recorded (Step 725). The velocity error is related to the sensitivity of apparatus 30, and thus may be pre-selected. Alternately, position or torque may be tracked and error checked. A sensitivity too high or too low may either break rod 90 (too low), or result in an inaccurate measurement or, more seriously, calibration location due to mechanical noise in the motion (too high). After the origin location of rod 90 is determined and recorded, controller 100 may send a command to motor 50, so that motor 50 may retract rod 90 to a predetermined park location (Step 730). The predetermined park location may be a pre-set distance above the origin location, for example, 1.5 meter above the origin location. The pre-set distance may be a fixed value and may be programmed into controller 100. Consistent with an embodiment, the pre-set distance may also change, for example, depending on different locations of solid-liquid interface 63 measured during a melting process.

After system 10 is calibrated according to calibration process 700, crucible 60 may be placed into vessel 20. The thickness of crucible 60 may be a known parameter, or may be measured. Seeds (not shown) may also be placed at the bottom of crucible 60. The thickness of seeds may be measured, or may be a known parameter. The thickness of crucible 60 and seeds at the bottom of crucible 60 may be programmed into controller 100. Solid material 64, such as silicon, may be placed on top of the seeds. Vessel 20 may be evacuated and may be ready for casting.

Figure 13:
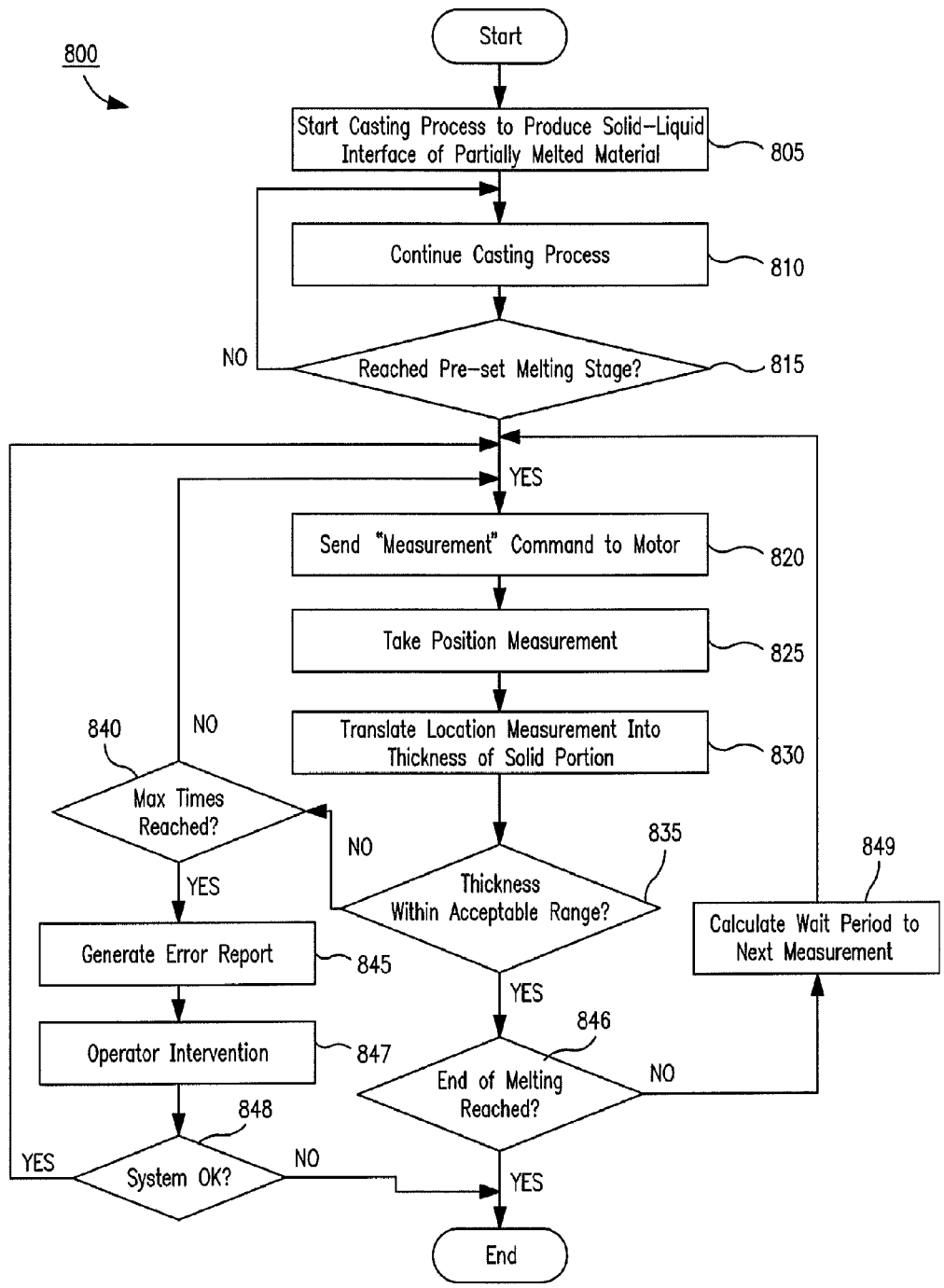
FIG. 13 illustrates an exemplary method for monitoring a solid-liquid interface in a partially melted material, according to an embodiment of the present invention.

FIG. 13 illustrates an exemplary monitoring process 800 during casting. First, system 10 starts melting solid material 64 by heating element 125 to produce a solid-liquid interface 63 (Step 805). Then system 10 continues to melt solid material 64 according to a predetermined melting program recipe (Step 810). For example, the melting program recipe may include stages of MELT 1, MELT 2, ..., MELT 12, etc. Among MELT 1-12, the early stages, for example, stages from MELT 1-MELT 8, may be configured to continuously increase the melting temperature inside the crucible, prior to insertion of rod 90 into fluid material. Then at a pre-set stage, for example, MELT 9, location measurements of solid-liquid interface 63 may begin. Next, one may determine whether a pre-set melting stage has been reached (Step 815). If the pre-set melting stage (e.g., MELT 9) has not been reached (NO, Step 815), system 10 may continue to melt the material (Step 810). If the pre-set melting stage (e.g., MELT 9) has been reached (YES, Step 815), controller 100 may send a "measurement" command to motor 50 to start the motor and begin the measuring process (Step 820). Rod 90 may be lowered, by motor 50, pinions 202 and 204, and rotating wheel 200, to approach solid-liquid interface 63. As rod 90 contacts solid-liquid interface 63, and as the predetermined velocity error (defined in calibration process 700) is detected by controller 100, controller 100 may send a command to motor 50 to stop the motor, thereby stopping further movement of rod 90. Then the location of rod 90 may be measured and recorded by controller 100 (Step 825).

This location measurement may be translated into a location of solid-liquid interface 63, or further, the thickness of solid material 64 (Step 830). The translation may be performed by controller 100 based on the measured location of rod 90, the calibrated origin location of rod 90, and the known thickness of crucible 60 and the seeds at the bottom of the crucible, as well as a total length of rod 90. After the thickness of solid material 64 is calculated, controller 100 may send a command to motor 50 to retract rod 90 to the predetermined park location. A rapid process is crucial in this part of the operation to prevent interference with the solid/liquid system and to preserve the integrity of the rod 90. Controller 100 may determine whether the thickness of solid material 64 is within a pre-set acceptable range based on previous measurements (Step 835), for example, within 11 cm. If the thickness of solid material 64 is not within the pre-set acceptable range (NO, Step 835), controller 100 may further determine whether to repeat the same measurement and whether or not the number of attempts has exceeded a predetermined number (Step 840), for example, 3 times. If the number of attempts has not exceeded the predetermined number (NO, Step 840), Steps 820-830 may be repeated to obtain a one or more subsequent measurements of the thickness of solid material 64. If the number of attempted measurements has exceeded the predetermined number (YES, Step 840), an error report may be generated (Step 845), and the monitoring process may trigger an alarm and pause itself pending operator intervention (Step 847). Further actions, for example, inspection of apparatus 30 or restoration of calibration may then be conducted (Step 847) to diagnose potential causes associated with measured thicknesses outside the acceptable range. If the operator intervention finds no issues with the system 10 (Yes, Step 848), the monitoring process 800 may continue to repeat the measurement steps (Steps 820-835). If issues are found with the system 10 (NO, Step 848), the monitoring process 800 may be terminated. On the other hand, if the thickness of solid material 64 is within a pre-set acceptable range (YES, Step 835), the monitoring process 800 may determine whether it is the end of the melting process (Step 846). If it is not the end of the melting process (NO, Step 846), the system 10 may calculate a wait period to next measurement (Step 849), and then may go back to step 820. The wait period may be determined in the following way, or any equivalent manner. One or more regimes may be defined, each corresponding to a given waiting interval, based on time elapsed in the program or based directly on the measurements coming from the monitoring system. For example, a 30 minute wait period may be defined and used in the process until the overall process is completed more than 50% (based on measurements of the rod 90). Then a 15 minute wait period may be used until a 75% completion. After 75% completion, a 5 minute wait period may be used until the process is complete. To achieve greater accuracy, logic may be implemented during the final 25% of the overall process. The implemented logic may be programmed to predict the exact minutes to the end of the process based on previous measurements taken from the beginning of the process to the 75% completion of the process. When the predicted minutes are shorter than a default number (e.g., 5 minutes), the predicted minutes are used as the wait period in order to take a precise measurement at the end of the process. If it is the end of the melting process (YES, Step 846), the system 10 may trigger new stages in the casting recipe and may change its own function setting, for example by turning itself off. The monitoring process 800 may be ended, and a growth process may start subsequently after the melting process is ended.

The measurement steps, including Steps 820-849, may be repeated at a predetermined time interval, for example, every 20 minutes, during a melting stage. By combining several location measurements with a time period, it is possible to determine a rate of change in the location of solid-liquid interface, which may be used to calculate a melting rate. Melting stage MELT 9 may last for a predetermined time, for example, 120 minutes. During the predetermined time, an interval for taking a measurement may be changed, for example, from every 20 minutes to every 10 minutes, based on the thickness of solid material 64, or the heating temperature, for example. When the thickness of solid material 64 reaches a pre-set thickness, for example, 7 cm, melting stage may be transferred from one stage to another, for example, from MELT 9 to MELT 10. The transfer may be automated by programming controller 100. Melting stage MELT 10 may last for a predetermined time, for example, 20 minutes and may cause changes in heating and/or cooling rates or other parameters. Measurement Steps 820-849 may be repeated for stage MELT 10 at a predetermined time interval, for example, at every 5 minutes. As the melting rate slows, the time interval for taking measurements may be changed accordingly. At a certain melting stage, for example, MELT 12, the crystal growth process may begin. While solid-liquid interface could be monitored during the crystal growth stage, it is usually not so as to avoid introducing defects into the growing crystal.

It is understood that system 10 may lose calibration under some circumstances. Loss of calibration may be detected by controller 100, for example, when anomalous location data is acquired or when an error report is generated (Step 845). System 10 may restore its calibration by repositioning rod 90 to its park location. Various methods may be used to restore calibration. Two exemplary methods will be discussed.

Figure 14:
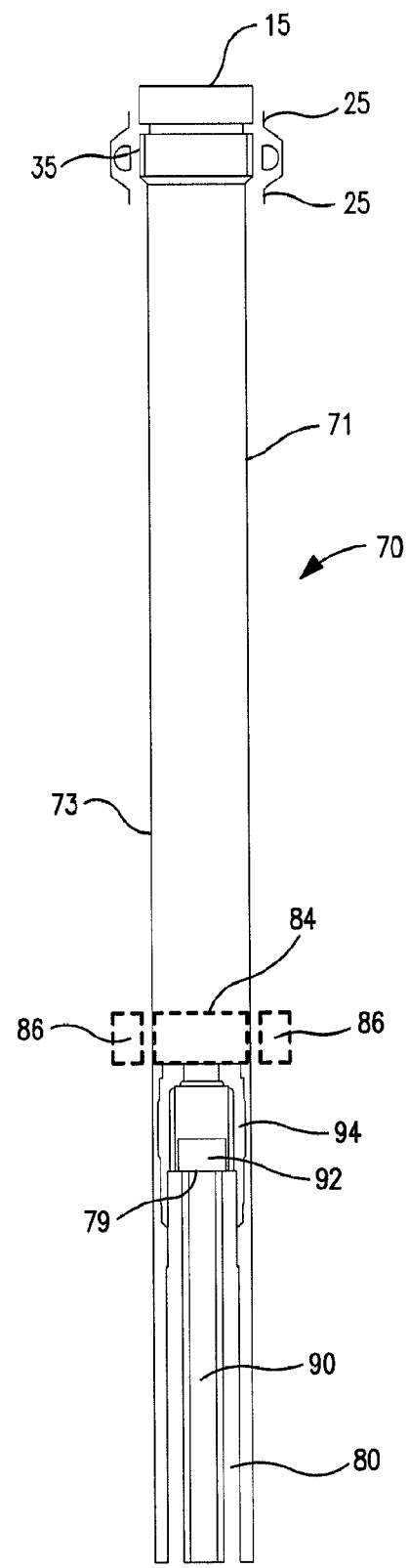
FIG. 14 illustrates, in cross section, a portion of a system for monitoring a solid-liquid interface in a partially melted material, according to an embodiment of the present invention.

FIG. 14 shows a cross-sectional view of tube 70 and the first method of restoring calibration using magnetic elements 86. As mentioned previously, tube 70 may at least partially enclose rack 80, where rod 90 is enclosed. Rod 90 may include a rod head 92 resting on an end 79 of rack 80. A retaining screw cap 94, or a cap, may be provided to secure rod head 92 to rack 80. Retaining screw cap 94 may be mounted to rod head 92 and rack 80 through any known method in the art. When the joint section between first portion 71 and second portion 72 of tube 70 is disassembled, as discussed previously, second portion 72 may be removed to expose retaining screw cap 94 and rack 80. To replace or install rod 90, retaining screw cap 94 may have to be removed first.

As shown in FIG. 14, apparatus 30 may include a first magnetic element 84 attached, or mounted, to retaining screw cap 94. One or more second magnetic elements 86 may be attached to an outer surface 73 of tube 70. Consistent with an embodiment, there may be a plurality of magnetic elements 86, for example, in form of stripes distributed around the outer surface 73. The location of second magnetic element 86 may be adjacent to that of first magnetic element 84. The first and second magnetic elements 84 and 86 may be configured so that when first magnetic element 84 is moved to a new location inside tube 70, second magnetic element 86 may also move to a new location along outer surface 73 of tube 70 due to the magnetic forces between these two elements. Therefore, the exact location of first magnetic element 84, which is not visible by an operator due to its location inside tube 70, may be indicated by second magnetic element 86, which is visible from the outside of tube 70. It is contemplated that there may be reference marks on the outer surface 73 of tube 70 to indicate the location of second magnetic element 86, and subsequently, the location of first magnetic element 84. From the known dimensions of rod 90, rack 80 and tube 70, retaining screw cap 94, first and second magnetic elements 84 and 86, and the location of first magnetic element 84, the location of rod 90 may be calculated. Moving the first magnetic element 84 may be achieved through motor 50, pinions 202, 204, and rotating wheel 200, as discussed above with respect to FIGS. 3-4.

Figure 15:
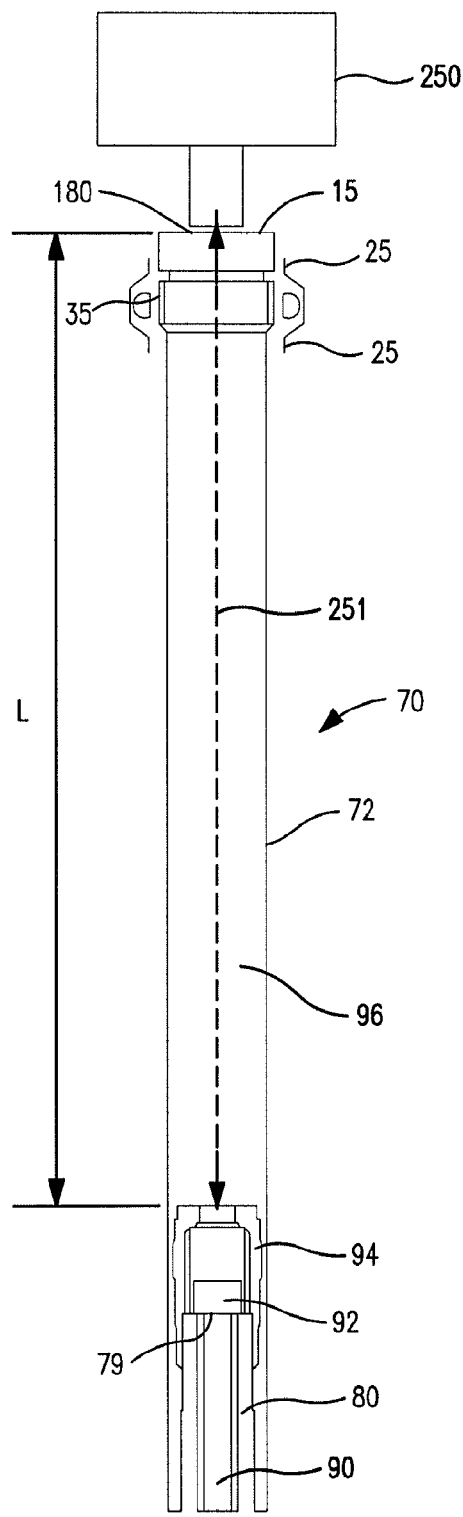
FIG. 15 illustrates, in cross section, a portion of a system for monitoring a solid-liquid interface in a partially melted material, according to an embodiment of the present invention.

FIG. 15 illustrates another method of restoring calibration, using device 250 disposed adjacent to window 180 at the end 15 of tube 70. Device 250 may produce a wave 251, such as a sonic wave, a light wave, etc., into a space 96 between window 180 and retaining screw cap 94. Therefore, device 250 may be a sonic device, an optical device, or other suitable device that can produce a wave. When wave 251 produced by device 250 travels in space 96 and encounters retaining screw cap 94, wave 251 may be reflected back to device 250. Device 250 may then detect the reflected wave 251. During this process, some characteristics of wave 251 may be changed. Device 250 may measure at least one parameter associated with the changed characteristics of wave 251. Then, a distance (L) of space 96 may be calculated based on the at least one parameter measured by device 250, according to a known relationship. From the calculated distance (L) of space 96, the location of rod 90 may be further calculated. In some embodiments, device 250 may be associated with controller 100, and may send measured parameter data to controller 100 for analysis and calculation of the location of rod 90. The at least one parameter of wave 251 may be a frequency, a phase shift, or a time of travel of the wave inside space 96.

For example, when a light or sonic wave 251 is reflected back to device 250, its frequency may be changed, or its phase may be shifted. From a known relationship between distance (L) of space 96 and the changes in frequency or phase shift of wave 251, the distance (L) of space 96 may be calculated. For another example, a pulse light or sonic wave may be generated and emitted by device 250 into space 96. When reflected back by retaining screw cap 94 and detected by device 250, the frequency shift or phase change of wave 251 inside space 96 may be determined by device 250, or by controller 100, which may be associated with device 250. From the frequency shift or phase change of wave 251, and known speed of wave 251, the distance (L) of space 96 may be calculated. From the calculated distance (L) of space 96, the location of rod 90 may be further calculated. Therefore, rod 90 may be repositioned to the calibrated origin location. In some embodiments, device 250 may be associated with controller 100, and may send measured parameters to controller 100 for further analysis and calculation. Consistent with an embodiment, device 250 may not be associated with controller 100, but instead, may be a stand-alone device, and may be configured to include a data processor to perform the measurement and calculation.

Figure 16:
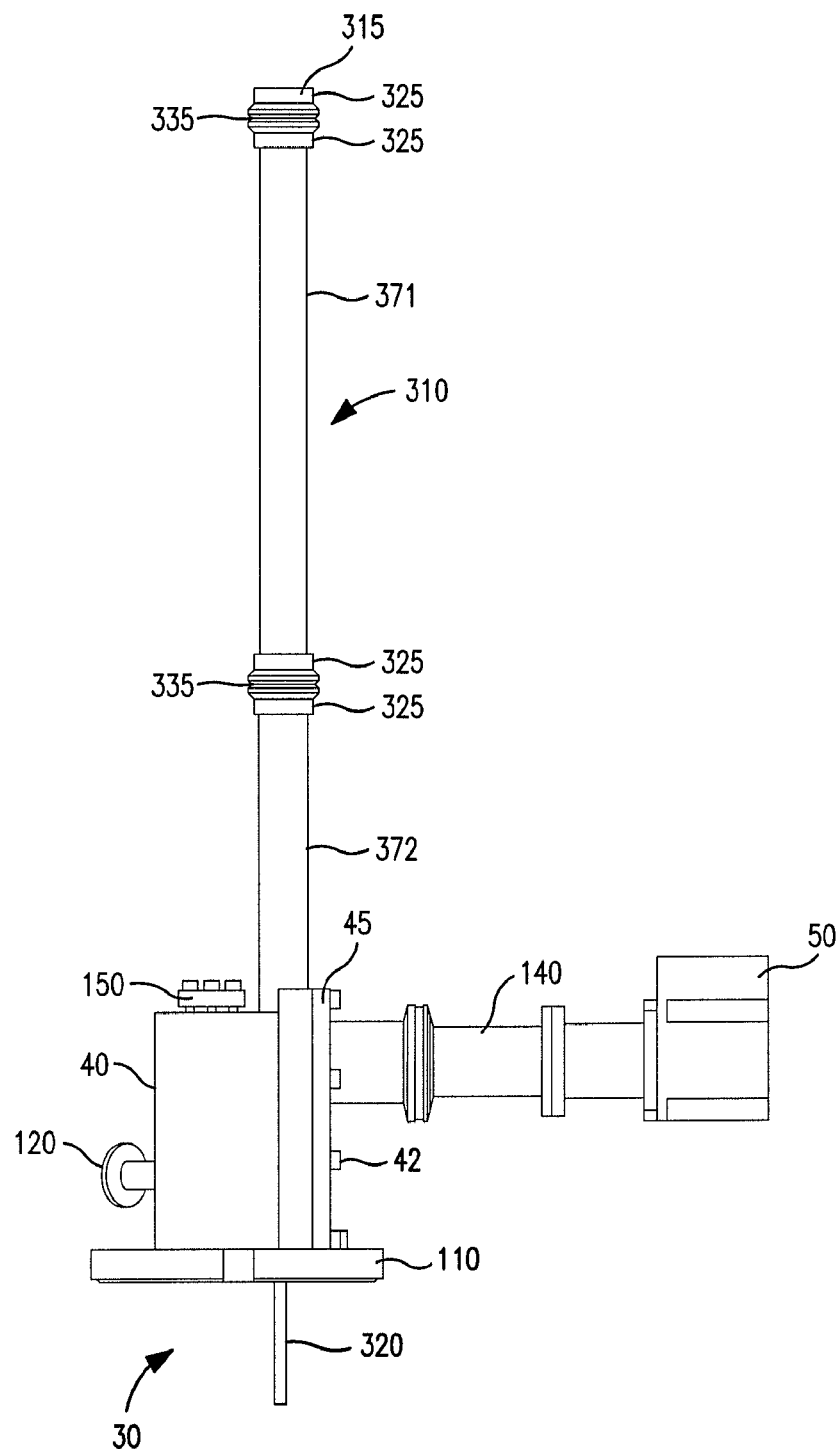
FIG. 16 illustrates a sectional view of an exemplary apparatus employed in a system for monitoring a solid-liquid interface in a partially melted material, according to an embodiment of the present invention.
Figure 17:
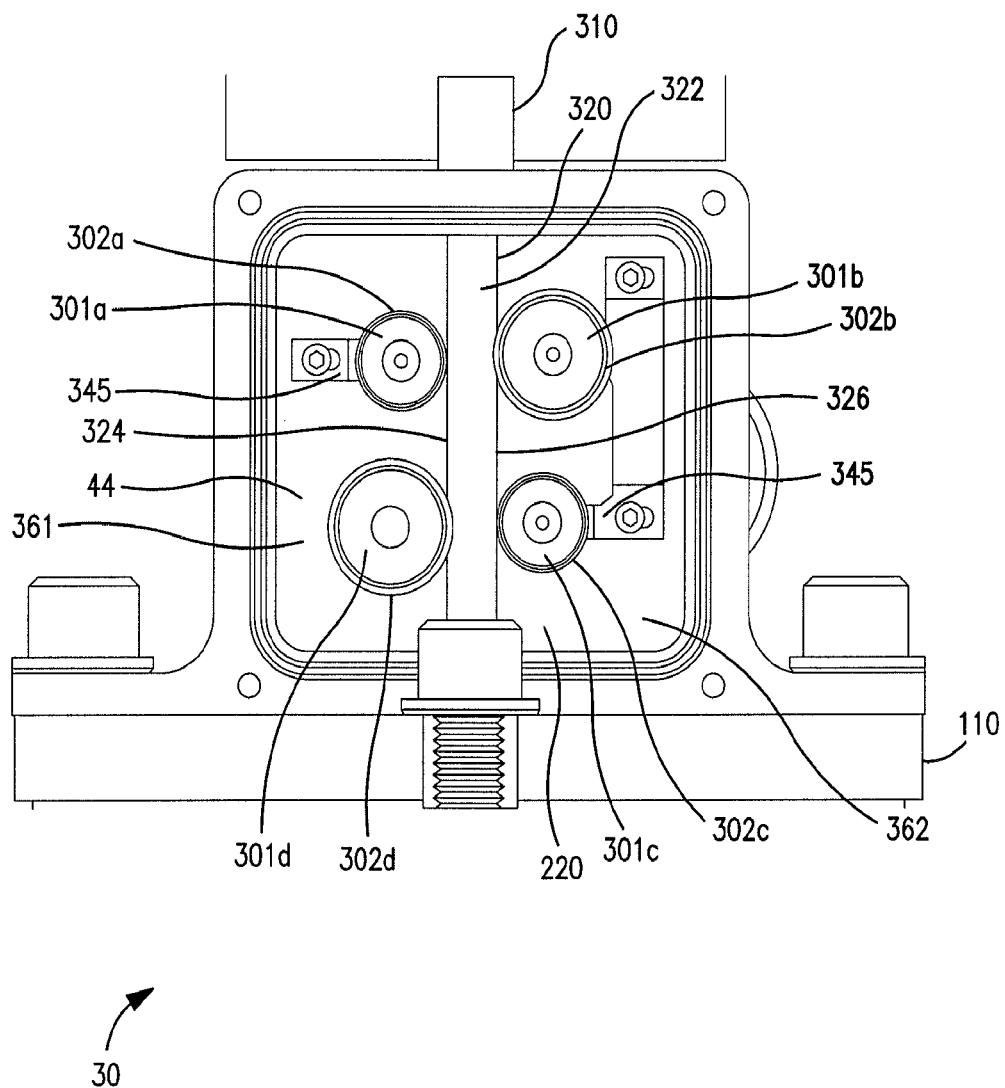
FIG. 17 illustrates, in cross section, a portion of a system for monitoring a solid-liquid interface in a partially melted material, according to an embodiment of the present invention.

Also consistent with an embodiment, FIG. 16 illustrates a sectional view of apparatus 30. FIG. 17 shows a partial cross-sectional view of apparatus 30 with a configuration of wheels, differing from that shown in FIG. 4 by the contents of housing 40. Apparatus 30 may also include a tube 310 at least partially enclosing rod 320. Tube 310 may include a plurality of portions, such as a first portion 371 and a second portion 372. At the joint section between the first and second portions, and at a top end 315 of tube 310, there may be flanges 325 and O-ring sealing component 335. O-ring sealing components 335 may be the same as the O-ring sealing components 35 shown in FIG. 1. At least one portion, for example, first portion 371, may be removable to allow access to rod 320 inside tube 310. For example, flanges 325 at the joint section between the first and second portions may be disassembled, and first portion 371 may be taken off to expose rod 320 inside tube 310.

As illustrated in FIG. 17, apparatus 30 may include a plurality of rotating wheels, such as, rotating wheels 301*a*, 301*b*, 301*c*, and 301*d*, each configured to contact an outer surface 322 of a rod 320. As shown in FIG. 17, a portion of rod 320 that contacts the rotating wheels may not be enclosed by tube 310 in first chamber 220. Extending and retracting of rod 320 may be achieved via the plurality of wheels 301*a*, 301*b*, 301*c*, 301*d*. Consistent with an embodiment, wheels 301 may directly contact outer surface 322 of rod 320 and exert a pressure on rod 320. With proper selection of materials for rod 320 and wheel 301, the frictional force between wheels 301 and rod 320 may be large enough to prevent sliding of rod 320, ensuring a suitable gripping of rod 320 during extending and retracting. To further increase the frictional force exerted on rod 320 by wheels 301, wheels 301 may be supported by pre-loaded springs 345. Pre-loaded springs 345 may push wheels 301 against rod 320, thus may further increase the frictional force between rod 320 and wheels 301. Rod 320 may be moved up and down (or extended and retracted) as wheels 301 rotate. While locations of pre-loaded springs 345 are shown in FIG. 17, pre-loaded springs 345 may alternatively be located between a plate, such as, for example, a bracing plate, and side wall of chamber 220.

Figure 18:
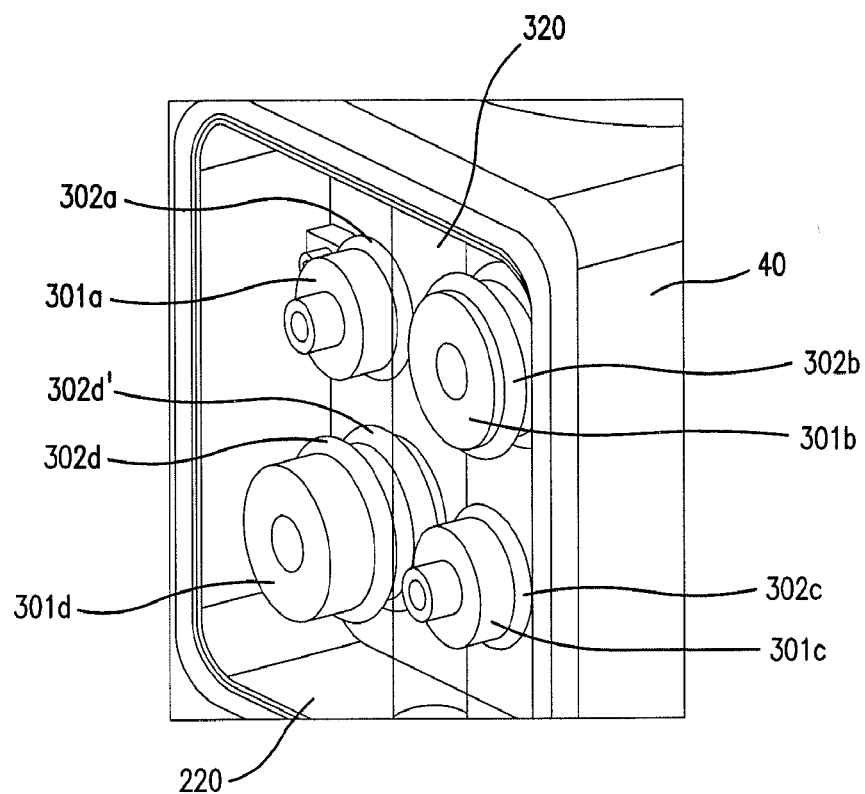
FIG. 18 illustrates a perspective view of a portion of a system for monitoring a solid-liquid interface in a partially melted material, according to an embodiment of the present invention.

Still referring to FIG. 17, wheels 301 may further include O-ring components, such as, 302*a*, 302*b*, 302*c*, and 302*d*, attached, or mounted to wheels 301. O-ring components 302 may improve gripping of rod 320 if contacting rod 320 through wheels 301 does not provide a sufficient frictional force to grip rod 320. O-ring components 302 may be mounted on wheels 301 through grooves on the surface of wheels, or may be otherwise mounted on the surface of wheels 301 by gluing. Consistent with an embodiment, a wheel, for example, 301*d*, as shown in FIG. 18, may include more than one O-ring component, for example, 302*d*, and 302*d'*. O-ring components 302 may exert a pressure on the outer surface 322 of rod 320, and may provide a proper gripping of rod 320. Rod 320 may thus be moved (extended and retracted) as wheels 301 rotate.

Consistent with an embodiment of the present invention, as shown in FIGS. 17 and 18, the plurality of wheels may include four wheels. A first pair of two wheels 301*a* and 301*d* are located on a first side 361 of rod 320, and are configured to contact a first surface 324 of rod 320. A second pair of two wheels 301*b* and 301*c* are located on a second side 362 of rod 320, and are configured to contact a second surface 326 of rod 320. Also as illustrated in FIGS. 17 and 18, wheels 301 may be of different diameter. For example, wheels 301*a* and 301*c* may have the same diameter, which may be smaller than the diameter of wheels 301*b* and 301*d*. As illustrated in FIG. 18, wheels 301*a* and 301*c* may include one O-ring component mounted on each wheel, wheels 301*b* and 301*d* may include more than one O-ring component mounted on each wheel.

O-ring components 302 may or may not be similar to O-ring sealing components 35 and 335 shown in FIG. 16.

Although wheels 301 are shown in FIGS. 17 and 18 located on the first wall 44 of first chamber 220, it is contemplated that, at least one of the wheels 301 may be located on second wall 45. Motor 50 may drive at least one of the wheels 301, for example, wheel 301*d*, through a motor shaft as shown in FIG. 5.

Figure 19:
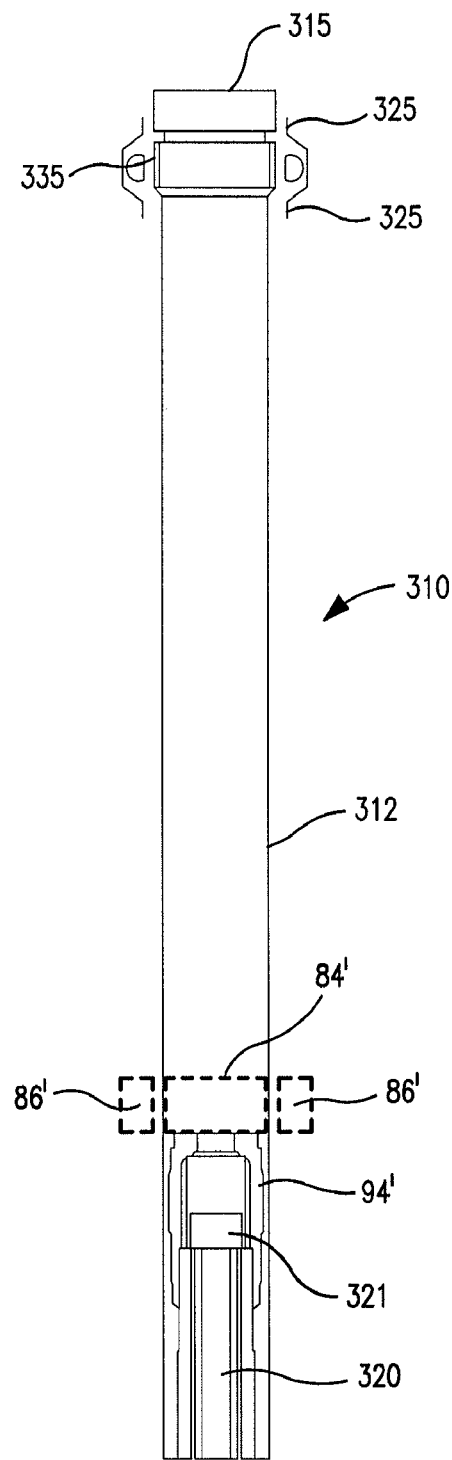
FIG. 19 illustrates, in cross section, a portion of a system for monitoring a solid-liquid interface in a partially melted material, according to an embodiment of the present invention.

FIG. 19 shows a cross-sectional view of tube 310 and a first method of restoring calibration using magnetic elements 86', similar to the method discussed with respect to FIG. 14. As mentioned previously, tube 310 may at least partially enclose rod 320. Rod 320 may include a rod head 321, where a retaining screw cap 94', or a cap, may be mounted. Retaining screw cap 94' may be mounted to rod head 321 through any known method in the art. As shown in FIG. 19, apparatus 30 may include a first magnetic element 84' attached, or mounted, to retaining screw cap 94'. One or more second magnetic elements 86' may be attached to an outer surface 312 of tube 310. Consistent with an embodiment of the present invention, there may be a plurality of magnetic elements 86', for example, in form of stripes distributed around the outer surface 312. The location of second magnetic element 86' may be adjacent to that of first magnetic element 84'. The first and second magnetic elements 84' and 86' may be configured so that when first magnetic element 84' is moved to a new location inside tube 310, second magnetic element 86' may also move to a new location along outer surface 312 of tube 310 due to the magnetic forces between these two elements. Therefore, the exact location of first magnetic element 84', which is not visible by an operator due to its location inside tube 310, may be indicated by second magnetic element 86', which is visible from the outside of tube 310. It is contemplated that there may be reference marks on the outer surface 312 of tube 310 to indicate the location of second magnetic element 86', and subsequently, the location of first magnetic element 84'. From the known dimensions of rod 320, tube 310, retaining screw cap 94', first and second magnetic elements 84' and 86', and the location of first magnetic element 84', the location of rod 320 may be calculated. Moving the first magnetic element 84' may be achieved through motor 50 and the plurality of rotating wheels 301, as discussed above with respect to FIGS. 16-17.

Figure 20:
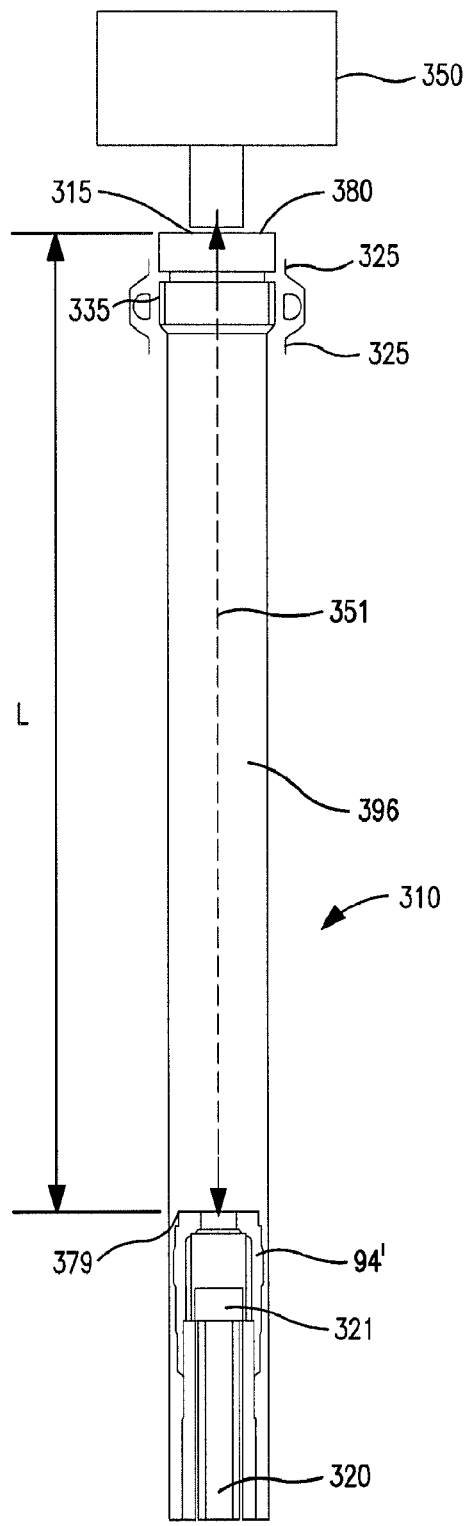
FIG. 20 illustrates, in cross section, a portion of a system for monitoring a solid-liquid interface in a partially melted material, according to an embodiment of the present invention.

FIG. 20 illustrates a second method of restoring calibration, similar to the method discussed in the embodiment shown in FIG. 15. Device 350 may be disposed adjacent to window 380 at the end 315 of tube 310. Device 350 may produce a wave 351, such as a sonic wave, a light wave, etc., into a space 396. Consistent with an embodiment, space 396 may be the space between window 380 and retaining screw cap 94'. Consistent with another embodiment, retaining screw cap 94' may not be needed at rod head 321. In such an embodiment, space 396 will be the space between window 380 and rod head 321. For convenience, space 396 is referred to as a space between window 380 and an end 379 of rod 320, wherein end 379 may be referred to as retaining screw cap 94' if retaining screw cap 94' is present at rod head 321, or rod head 321 if retaining screw cap 94' is not present at rod head 321.

Device 350 may be a sonic device, an optical device, or other suitable device that can produce a wave. When wave 351 produced by device 350 travels in space 396 and encounters end 379, wave 351 may be reflected back to device 350. Device 350 may then detect the reflected wave 351. During this process, some characteristics of wave 351 may be changed. Device 350 may measure at least one parameter associated with the changed characteristics of wave 351. Then, a distance (L) of space 396 may be calculated based on the at least one parameter measured by device 350, according to a known relationship. From the calculated distance (L) of space 396, the location of rod 320 may be further calculated. Consistent with an embodiment, device 350 may be associated with controller 100, and may send measured parameter data to controller 100 for analysis and calculation of the location of rod 320. The at least one parameter of wave 351 may be a frequency, a phase shift, or a time of travel of the wave inside space 396. Consistent with another embodiment, device 350 may not be associated with controller 100, but instead, may be a stand-alone device, and may be configured to include a data processor to perform the measurement and calculation.

For example, when a light or sonic wave 351 is reflected back to device 350, its frequency may be changed, or its phase may be shifted. From a known relationship between distance (L) of space 396 and the changes in frequency or phase shift of wave 351, the distance (L) of space 396 may be calculated. For another example, a pulse light or sonic wave may be generated and emitted by device 350 into space 396. When reflected back by end 379 and detected by device 350, the time of travel of wave 351 inside space 396 may be determined by device 350, or by controller 100, which may be associated with device 350. From the time of travel of wave 351, and known speed of wave 351, the distance (L) of space 396 may be calculated. From the calculated distance (L) of space 396, the location of rod 320 may be further calculated. Therefore, rod 320 may be repositioned to the calibrated origin location. In some embodiments, device 350 may analyze the measured parameters, or may send measured parameters to controller 100 for further analysis and calculation. A predetermined threshold accuracy level in repositioning rod 90 or rod 320 may be satisfied in order to restore calibration using the embodiments discussed in FIGS. 14-15, or FIGS. 19-20. The threshold accuracy level may be any desired level based on practical needs. Consistent with an embodiment, the predetermined threshold accuracy level may be 0.5 mm or smaller.

When operating the disclosed system 10 for monitoring the solid-liquid interface of a material during a casting process, the tip of rod 90, or 320, which may be made of quartz, may experience considerably high temperature, for example, 1550° C. or higher. Consistent with an embodiment, the tip of rod 90 or 320 may be about 1 m from the bottom of the plate 110, or from the bottom of rack 80 when rack 80 and pinions 202 and 204 are used. Therefore, for example, in the embodiment discussed in FIGS. 4-5, the temperature around the bottom of rack 80 may be about 300° C. Depending on the material property of rack 80, this temperature at the bottom of rack 80 may be high enough to affect the motion of rack 80. Furthermore, when rack 80 is machined for tooth-shaped components 82 before rack 80 is assembled to apparatus 30 and used for monitoring solid-liquid interface, there may be stresses left in rack 80 during the machining process. Due to thermal cycling effect caused by the high temperature at the bottom of rack 80, or the existing stresses in rack 80, or the combined effects of both thermal cycling and existing stresses, rack 80 may warp during its motion, and thus may not be able to extend rod 90 in a desired straight direction. This issue may be solved by selecting a material which does not cause stresses when being machined, or the stress within which can be relieved for making rack 80. Additionally, a material that can tolerate sufficiently high temperature may also be selected for rack 80.

It will be apparent to those skilled in the art that various modifications and variations can be made in the disclosed systems and methods without departing from the scope or spirit of the invention. Although casting of silicon has been primarily described herein, other semiconductor materials and nonmetallic crystalline materials may be cast without departing from the scope and spirit of the invention. For example, casting of other materials is possible, such as gallium arsenide, silicon germanium, aluminum oxide, gallium nitride, zinc oxide, zinc sulfide, gallium indium arsenide, indium antimonide, germanium, yttrium barium oxides, lanthanide oxides, magnesium oxide, and other semiconductors, oxides, and intermetallics with a liquid phase. It will now be apparent to one of ordinary skill in the art that a solid-liquid interface of any material including any metal with a liquid phase could be characterized by the above described systems and methods. These metals and semimetals may include, for example, Al, Si, P, S, Zn, Ga, Ge, GaAs, Se, Cd, In, Sn, Sb, Te, Hg, Pb, Fe, Ti, Pt, Au, Ag, Cr, Co, Ni, Cu, and Bi, as well as alloys, oxides or nitrides of these materials. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A system for monitoring a solid-liquid interface, comprising:
    a vessel configured to contain an at least partially melted material having a solid-liquid interface; and
    an apparatus attached to the vessel and including:
        a rod configured to measure a location of the solid-liquid interface;
        a pinion;
        a rack having a first portion of an outer surface configured to engage the pinion, and to at least partially enclose the rod;
        a tube configured to at least partially enclose the rack;
        a rotating wheel configured to contact a second portion of the outer surface of the rack;
        a motor configured to drive the pinion; and
        a controller configured to control the motor and monitor at least one parameter of the solid-liquid interface.

2. The system of claim 1, further comprising a housing, the housing having:
    at least one chamber containing at least a portion of the rack and the tube; and
    a removable wall covering a side of the at least one chamber.

3. The system of claim 2, wherein the at least one chamber contains the pinion, the wheel, and at least a portion of the rack, and includes a window mounted thereon to allow observation of the inside of the vessel.

4. The system of claim 3, wherein at least one of the pinion and the rotating wheel is located on a wall of the at least one chamber.

5. The system of claim 3, wherein at least one of the pinion and the rotating wheel is located on the removable wall.

6. The system of claim 3, wherein the motor is configured to drive the pinion through a motor shaft.

7. The system of claim 1, wherein the tube further includes a window mounted at an end of the tube.

8. The system of claim 7, further including a retaining screw cap Located inside the tube and mounted on an end of the rack to removably secure the rod to the end of the rack.

9. The system of claim 8, further including a first magnetic element mounted on the retaining screw cap and a second magnetic element attached to an outer surface of the tube, wherein the first magnetic element mounted on the retaining screw cap is movable inside the tube, and the second magnetic element is movable consistent with the first magnetic element.

10. The system of claim 8, further including a device mounted adjacent to the window, being configured to measure a dimension of a space inside the tube.

11. The system of claim 10, wherein the device is a sonic device configured to produce a sound wave traveling inside the space, and wherein the dimension of the space is measured based on at least one parameter associated with the sound wave.

12. The system of claim 10, wherein the device is an optical device configured to produce a light wave traveling inside the space, and wherein the dimension of the space is measured based on at least one parameter associated with the light wave.

13. The system of claim 2, wherein the housing is mounted on a plate having a plurality of hollow zones associated with the at least one chamber, and wherein the plate is configured to cover a port of the vessel.

14. The system of claim 1, wherein the tube is configured to include a plurality of portions, and at least one portion is configured to allow access to the rack and the rod.

15. The system of claim 1, wherein the at least one parameter of the solid-liquid interface includes at least one of a location of the solid-liquid interface and a rate of change in the location.

16. The system of claim 15, wherein the controller is further configured to calculate at least one of the thickness of the solid portion and the rate of change in the thickness of the solid portion.

17. The system of claim 1, wherein the pinion is a first pinion, the system further includes at least a second pinion engaged with the rack.

18. The system of claim 2, wherein the at least one chamber includes a first open port and a second open port, wherein the portion of the rack enters the at least one chamber through the first open port, and extends to the top of the at least one chamber through the second open port.

19. The system of claim 18, wherein the at least one chamber hi-ther includes a third open port associated with an inlet.

20. The system of claim 1, wherein the rod is made of quartz.

21. The system of claim 1, further including a crucible configured to contain the at least partially melted material and enclosed by the vessel.

22. The system of claim 1, wherein the vessel includes at least one hot side wall surface in contact with crucible containing the at least partially melted material, the hot side wall surface being isothermal with or hotter than the at least partially melted material.

23. A system for monitoring a solid-liquid interface, comprising:
    a vessel configured to contain an at least partially melted material having a solid-liquid interface; and
    an apparatus attached to the vessel and including:
        a rod configured to measure a location of the solid-liquid interface;
        a tube configured to at least partially enclose the rod;
        a plurality of rotating wheels configured to contact an outer surface of the rod;
        a motor configured to drive at least one of the plurality of rotating wheels; and
        a controller configured to control the motor and monitor at least one parameter of the solid-liquid interface.

24. The system of claim 23, further comprising a housing, the housing including:
   at least one chamber containing at least a portion of the rack and the tube; and
   a removable wall covering a side of the at least one chamber.

25. The system of claim 24, wherein the at least one chamber contains the wheels and at least a portion of the rod, and the at least one chamber includes a first and a second open port, and a window mounted adjacent to the first open port to allow observation of the inside of the vessel.

26. The system of claim 24, wherein at least one of the rotating wheels is located on the a wall of the at least one chamber.

27. The system of claim 24, wherein at least one of the rotating wheels is located on the removable wall.

28. The system of claim 24, wherein the motor is configured to drive at least one of the plurality of rotating wheels through a motor shaft.

29. The system of claim 23, wherein the tube further includes a window mounted at an end of the tube.

30. The system of claim 29, further including a retaining screw cap located inside the tube and mounted on a head of the rod.

31. The system of claim 30, further including a first magnetic element mounted on the retaining screw cap and a second magnetic element attached to an outer surface of the tube, wherein the first magnetic element mounted on the retaining screw cap is movable inside the tube, and the second magnetic element is movable consistent with the first magnetic element.

32. The system of claim 30, further including a device mounted adjacent to the window, being configured to measure a dimension of a space inside the tube.

33. The system of claim 32, wherein the device is a sonic device configured to produce a sound wave traveling inside the space, and wherein the dimension of the space is measured based on at least one parameter associated with the sound wave.

34. The system of claim 32, wherein the device is an optical device configured to produce a light wave traveling inside the space, and wherein the dimension of the space is measured based on at least one parameter associated with the light wave.

35. The system of claim 24, wherein the housing is mounted on a plate having a plurality of hollow zones associated with the at least one chamber, and wherein the plate is configured to cover a port of the vessel.

36. The system of claim 23, wherein the tube is configured to include a plurality of portions, and at least one portion is configured to allow access to the rod.

37. The system of claim 23, wherein the at least one parameter of the solid-liquid interface includes at least one of a location of the solid-liquid interface and a rate of change in the location.

38. The system of claim 37, wherein the controller is further configured to calculate at least one of the thickness of the solid portion and the rate of change in the thickness of the solid portion.

39. The system of claim 23, wherein each of the plurality of rotating wheels includes at least one O-ring component.

40. The system of claim 23, wherein the motor is configured to drive at least one of the plurality of rotating wheels through a motor shaft.

41. The system of claim 24, wherein the at least one chamber includes a first and a second open port, wherein the portion of the rod enters the at least one chamber through the first open port, and extends outside of the at least one chamber through the second open port.

42. The system of claim 41, wherein the at least one chamber further includes a third open port associated with an inlet.

43. The system of claim 23, wherein the plurality of rotating wheels includes four rotating wheels, with a first pair of two rotating wheels located on a first side of the rod, contacting a first portion of the outer surface of the rod, and a second pair of two rotating wheels located on a second side of the rod, contacting a second portion of the outer surface of the rod.

44. The system of claim 23, wherein at least one of the plurality of rotating wheels is associated with a spring.

45. The system of claim 23, wherein the rod is made of quartz.

46. The system of claim 23, further including a crucible configured to contain the at least partially melted material and enclosed by the vessel.

47. The system of claim 46, wherein the vessel includes at least one hot side wall surface in contact with the at least partially melted material, the hot side wall surface being isothermal with or hotter than the at least partially melted material.

48. A method of monitoring a solid-liquid interface of an at least partially melted material with an apparatus including a rod, a rack at least partially enclosing the rod, and a pinion engaged with the rack, the method comprising:
   extending the rod to contact the solid-liquid interface;
   stopping the rod when the rod contacts the solid-liquid interface based on a threshold input;
   measuring a location of the rod when the rod is stopped;
   retracting the rod to a predetermined location; and
   calculating at least one parameter associated with the solid-liquid interface based on at least the measured location of the rod when the rod is stopped.

49. The method according to claim 48, further including calibrating the rod to establish an origin location of the rod.

50. The method according to claim 48, wherein calibrating the rod includes:
   sending a first command signal to a motor to drive the pinion and extend the rod;
   stopping the motor based on the threshold input when the rod contacts the solid-liquid interface;
   measuring a location of the rod when the motor is stopped;
   determining an origin location for the rod; and
   sending a second command signal to the motor to drive the pinion and retract the rod to a predetermined location.

51. The method according to claim 48, further including:
   detecting a loss of calibration of the rod; and
   restoring calibration of the rod by repositioning the rod to the calibrated origin location.

52. The method according to claim 51, wherein the apparatus further includes a tube at least partially enclosing the rack, and wherein repositioning the rod to the calibrated origin location includes:
   mounting a first magnetic element to a retaining screw cap mounted on the end of the rack;
   attaching a second magnetic element to an outer surface of the tube adjacent to the first magnetic element inside the tube;
   moving the first magnetic element by moving the rack and the rod; and
   determining the location of the first magnetic element by the location of the second magnetic element attached on the outer surface of the tube.

53. The method according to claim 51, wherein the apparatus further includes a tube at least partially enclosing the rack and having a window mounted on an end of the tube, and wherein repositioning the rod to the calibrated origin location includes:
mounting a device adjacent to the window on the end of the tube;
producing a wave traveling inside a space between the window and the end of the rack;
measuring at least one parameter associated with the wave;
determining a dimension of the space based on the measured at least one parameter; and
determining a location of the rack and the rod based on the determined dimension of the space.

54. The method according to claim 53, wherein the device is at least one of a sonic device and a optical device, and wherein the at least one parameter associated with the wave is at least one of a frequency, a phase shift, and a time of traveling of the wave.

55. The method according to claim 52, further including removably securing the rod to the rack at the end of the rack through the retaining screw cap.

56. The method according to claim 48, wherein extending and retracting the rod further includes:
engaging the pinion with a tube; and
driving the pinion by a motor.

57. The method according to claim 56, further including supporting the tube with a rotating wheel.

58. The method according to claim 48, wherein the apparatus further includes a housing having at least one chamber, the method further including observing the inside of a vessel containing the at least partially melted material.

59. The method according to claim 58, further including reducing the temperature of the at least one chamber with a cooling gas.

60. A method of monitoring a solid-liquid interface of an at least partially melted material contained in a vessel with an apparatus including a rod, a tube at least partially enclosing the rod, and a plurality of rotating wheels, the method comprising:
extending the rod to contact the solid-liquid interface;
stopping the rod when the rod contacts the solid-liquid interface based on a threshold input;
measuring a location of the rod when the rod is stopped;
retracting the rod to a predetermined location; and
calculating at least one parameter associated with the solid-liquid interface based on at least the measured location of the rod when the rod is stopped.

61. The method according to claim 60, further including calibrating the rod to establish an origin location of the rod based on a threshold input.

62. The method according to claim 61, wherein calibrating the rod includes:
sending a first command signal to a motor to drive the rotating wheels and extend the rod;
stopping the motor based on the threshold input when the rod contacts the solid-liquid interface;
measuring a location of the rod when the motor is stopped;
determining an origin location for the rod; and
sending a second command signal to the motor to drive the rotating wheels and retract the rod to a predetermined location.

63. The method according to claim 61, further including:
detecting a loss of calibration of the rod; and
restoring calibration of the rod by repositioning the rod to the calibrated origin location.

64. The method according to claim 63, wherein repositioning the rod to the calibrated origin location includes:
mounting a first magnetic element to a retaining screw cap mounted on a rod head;
attaching a second magnetic element to an outer surface of the tube adjacent to the first magnetic element inside the tube;
moving the first magnetic element by moving the rod; and
determining the location of the first magnetic element by the location of the second magnetic element attached on the outer surface of the tube.

65. The method according to claim 63, wherein repositioning the rod to the calibrated origin location includes:
mounting a device adjacent to the window on the end of the tube;
producing a wave traveling inside a space between the window and an end of the rod;
measuring at least one parameter associated with the wave;
determining a dimension of the space based on the measured at least one parameter; and
determining a location of the rack and the rod based on the determined dimension of the space.

66. The method according to claim 65, wherein the device is at least one of a sonic device and a optical device, and wherein the at least one parameter associated with the wave is at least one of a frequency, a phase shift, and a time of traveling of the wave.

67. The method according to claim 60, wherein extending and retracting the rod further includes:
securing the rod with the plurality of rotating wheels; and
driving at least one of the wheels by a motor.

68. The method according to claim 67, wherein securing the rod includes securing the rod with at least one O-ring component mounted on the plurality of rotating wheels.

69. The method according to claim 67, wherein securing the rod includes exerting a force on the wheels against the rod with pre-loaded springs.

70. The method according to claim 60, wherein the apparatus further includes a housing having at least one chamber, the method further including observing the inside of a vessel containing the at least partially melted material.

71. The method according to claim 70, further including reducing the temperature of the at least one chamber with a cooling gas.

* * * * *